(12) United States Patent
Chen et al.

(10) Patent No.: US 7,815,905 B2
(45) Date of Patent: *Oct. 19, 2010

(54) METHODS OF INCREASING INSULIN SENSITIVITY OR DECREASING INSULIN SECRETION BY ADMINISTERING CORTICOTROPIN RELEASING FACTOR RECEPTOR-2 INHIBITORS

(75) Inventors: Alon M. Chen, Rehovot (IL); Kuo-Fen Lee, Del Mar, CA (US); Chien Li, Charlottesville, VA (US); Wylie W. Vale, La Jolla, CA (US)

(73) Assignee: Research Development Foundation, Carson City, NV (US)

( * ) Notice: Subject to any disclaimer, the term of this patent is extended or adjusted under 35 U.S.C. 154(b) by 295 days.

This patent is subject to a terminal disclaimer.

(21) Appl. No.: 11/668,047

(22) Filed: Jan. 29, 2007

(65) Prior Publication Data

US 2008/0161235 A1 Jul. 3, 2008

Related U.S. Application Data

(60) Provisional application No. 60/762,906, filed on Jan. 27, 2006.

(51) Int. Cl.
*A61K 39/395* (2006.01)
*A61K 39/00* (2006.01)
(52) U.S. Cl. .................................. 424/130.1; 424/139.1
(58) Field of Classification Search ........................ None
See application file for complete search history.

(56) References Cited

U.S. PATENT DOCUMENTS

| | | | | |
|---|---|---|---|---|
| 5,109,111 | A | 4/1992 | Rivier et al. | 530/306 |
| 5,245,009 | A | 9/1993 | Kornreich et al. | 530/306 |
| 5,510,458 | A | 4/1996 | Kornreich et al. | 530/306 |
| 5,777,073 | A | 7/1998 | Rivier | 530/306 |
| 5,874,227 | A | 2/1999 | Rivier | 435/7.1 |
| 6,323,312 | B1 | 11/2001 | Rivier | 530/306 |
| 6,670,140 | B2 | 12/2003 | Isfort et al. | 435/7.24 |
| 6,680,367 | B1 * | 1/2004 | Desjardins et al. | 530/350 |
| 6,812,210 | B2 | 11/2004 | Vale et al. | 514/12 |
| 6,953,838 | B2 | 10/2005 | Vale et al. | 530/350 |
| 2002/0082409 | A1 | 6/2002 | Hsu et al. | 536/23.5 |
| 2002/0183375 | A1 * | 12/2002 | Dubowchik et al. | 514/393 |
| 2004/0034882 | A1 * | 2/2004 | Vale et al. | 800/18 |
| 2006/0069516 | A1 | 3/2006 | Royappa | 702/19 |
| 2007/0042954 | A1 | 2/2007 | Chen et al. | 514/12 |

FOREIGN PATENT DOCUMENTS

| | | |
|---|---|---|
| EP | 1097709 | 5/2001 |
| WO | WO 02/24732 | 3/2002 |
| WO | WO 02/074326 | 9/2002 |
| WO | WO 03/062277 | 7/2003 |
| WO | WO 2006/086402 | 8/2006 |

OTHER PUBLICATIONS

Bale et al., "Corticotropin-Releasing Factor Receptor-2-Deficient Mice Display Abnormal Homeostatic Responses to Challenges of Increased Dietary Fat and Cold," *Endocrinology*, 144:2580-2587, 2003.
Brar et al., "Urocortin-II and Urocortin-III Are Cardioprotective against Ischemia Reperfusion Injury: An Essential Endogenous Cardioprotective Role for Corticotropin Releasing Factor Receptor Type 2 in the Murine Heart," *Endocrinology*, 145(1):24-35, 2004.
Chalmers et al., "Localization of novel corticotropin-releasing factor receptor (CRF2) mRNA expression to specific subcortical nuclei in rat brain: comparison with CRF1 receptor mRNA expression ," *J. Neuroscience*, 15:6340-6350, 1995.
Chen et al., "Mouse corticotropin-releasing factor receptor type 2alpha gene: isolation, distribution, pharmacological characterization and regulation by stress and glucocorticoids," *Mol. Endocrinol.*, 19:441-458, 2005.
Chen et al., "Urocortin II gene is highly expressed in mouse skin and skeletal muscle tissues: localization, basal expression in corticotropin-releasing factor receptor (CRFR) 1- and CRFR2- null mice, and regulation by glucocorticoids," *Endocrinology*, 145:2445-2457, 2004.
Cullen et al., "Urocortin corticotropin releasing factor-2 receptors and energy balance," *Endocrinology*, 142:992-999, 2001.
Florence and Yeager, "Treatment of Type 2 Diabetes Mellitus," *American Family Physician, AAFP*, 1999.
Gilon & Henquin, "Mechanisms and physiological significance of the cholinergic control of pancreatic beta-cell function," *Endocr. Rev.*, 22:565-604, 2001.
Hsu and Hsueh, "Human stresscopin and stresscopin-related peptide are selective ligands for the type 2 corticotropin-releasing hormone receptor," *Nat. Med.*, 7:605-611, 2001.
Kishimoto et al., "A sauvagine/corticotropin-releasing factor receptor expressed in heart and skeletal muscle," *Proc. Natl. Acad. Sci. USA*, 92:1108-1112, 1995.
Kostich et al., "Molecular Identification and Analysis of a Novel Human Corticotropin-Releasing Factor (CRF) Receptor: The $CRF_{2\gamma}$ Receptor," *Mol. Endo.*, 12(8):1077-1085, 1998.
Lewis et al., "Identification of urocortin III, an additional member of the corticotropin-releasing factor (CRF) family with high affinity for the CRF2 receptor," *PNAS*, 98(13):7570-7575, 2001.
NCBI Accession No. AF011406, "Homo sapiens corticotropin releasing hormone receptor type 2 beta isoform (CRH2R) mRNA, complete cds," 1997.

(Continued)

*Primary Examiner*—Robert Landsman
(74) *Attorney, Agent, or Firm*—Fulbright & Jaworski, L.L.P.

(57) ABSTRACT

In some aspects, the invention relates to methods for increasing insulin-sensitivity and/or decreasing insulin secretion in an individual by reducing or inhibiting corticotropin releasing factor 2 (CRFR2) signaling. CRFR2 antagonists may block agonism by one or more CRFR2 agonist, for example Ucn 2 or Ucn 3. Methods according to the invention may be use to treat a variety of metabolic diseases such as type 2 diabetes, metabolic syndrome, nonalcoholic fatty liver disease, polycystic ovarian syndrome and obesity.

16 Claims, 10 Drawing Sheets

OTHER PUBLICATIONS

PCT International Search Report and Written Opinion, issued in International Application No. PCT/US2007/061230, dated Oct. 11, 2007.

Perrin et al., "Identification of a second corticotropin-releasing factor receptor gene and characterization of a cDNA expressed in heart," *Proc. Natl. Acad. Sci. USA*, 92:2969-2973, 1995.

Reyes et al., "Urocortin II: a member of the corticotropin-releasing factor (CRF) neuropeptide family that is selectively bound by type 2 CRF receptors," *Proc. Natl. Acad. Sci. USA*, 98:2843-2848, 2001.

Rijkers et al., "Structure-activity studies on the corticotropin releasing factor antagonist astressin, leading to a minimal sequence necessary for antagonistic activity," *ChemBioChem*, 5(3)340-348, 2004.

Rivier et al., "Potent and Long-Acting Corticotropin Releasing Factor (CRF) Receptor 2 Selective Peptide Competitive Antagonists," *J. Med. Chem.*, 45:4737-4747, 2002.

Rivier et al., "Role of corticotropin-releasing factor receptors type 1 and 2 in modulating the rat adrenocorticotropin response to stressors," *Endocrinology*, 144:2396-403, 2003.

Shulman, "Cellular mechanisms of insulin resistance," *J. Clin. Invest.*, 106:171-176, 2000.

Shulman, "Unraveling the cellular mechanism of insulin resistance in humans: new insights from magnetic resonance spectroscopy," *Physiology*, 19:183-190, 2004.

Smith et al., "Corticotropin releasing factor receptor 1-deficient mice display decreased anxiety, impaired stress response, and aberrant neuroendocrine development," *Neuron.*, 20:1093-1102, 1998.

Virkamaki et al., "Protein-protein interaction in insulin signaling and the molecular mechanisms of insulin resistance," *J. Clin. Invest.*, 103:931-943, 1999.

Zierath et al., "Insulin action and insulin resistance in human skeletal muscle," *Diabetologia*, 43:821-835, 2000.

* cited by examiner

SEQUENCE LISTING

<160> NUMBER OF SEQ ID NOS: 31

<210> SEQ ID NO 1
<211> LENGTH: 38
<212> TYPE: PRT
<213> ORGANISM: Homo sapiens

<400> SEQUENCE: 1

Ile Val Leu Ser Leu Asp Val Pro Ile Gly Leu Leu Gln Ile Leu Leu

```
                 1               5                  10                 15
Glu Gln Ala Arg Ala Arg Ala Ala Arg Glu Gln Ala Thr Thr Asn Ala
                20                  25                 30

Arg Ile Leu Ala Arg Val
         35

<210> SEQ ID NO 2
<211> LENGTH: 38
<212> TYPE: PRT
<213> ORGANISM: Homo sapiens

<400> SEQUENCE: 2

Phe Thr Leu Ser Leu Asp Val Pro Thr Asn Ile Met Asn Leu Leu Phe
 1               5                  10                 15

Asn Ile Ala Lys Ala Lys Asn Leu Arg Ala Gln Ala Ala Ala Asn Ala
                20                  25                 30

His Leu Met Ala Gln Ile
         35

<210> SEQ ID NO 3
<211> LENGTH: 38
<212> TYPE: PRT
<213> ORGANISM: Mus musculus

<400> SEQUENCE: 3

Phe Thr Leu Ser Leu Asp Val Pro Thr Asn Ile Met Asn Ile Leu Phe
 1               5                  10                 15

Asn Ile Asp Lys Ala Lys Asn Leu Arg Ala Lys Ala Ala Ala Asn Ala
                20                  25                 30

Gln Leu Met Ala Gln Ile
         35

<210> SEQ ID NO 4
<211> LENGTH: 38
<212> TYPE: PRT
<213> ORGANISM: Mus musculus

<400> SEQUENCE: 4

Val Ile Leu Ser Leu Asp Val Pro Ile Gly Leu Leu Arg Ile Leu Leu
 1               5                  10                 15

Glu Gln Ala Arg Tyr Lys Ala Ala Arg Asn Gln Ala Ala Thr Asn Ala
                20                  25                 30

Gln Ile Leu Ala His Val
         35

<210> SEQ ID NO 5
<211> LENGTH: 1546
<212> TYPE: DNA
<213> ORGANISM: Homo sapiens

<400> SEQUENCE: 5
gtagtgcctg ccccagccc caggcagcca cagcaggctg ccttacccca gaagcagctg      60
gtggcgcctg acctcacgat gaccaggtgt gctctgctgt tgctgatggt cctgatgttg     120
ggcagagtcc tggttgtccc agtgacccct atcccaacct tccagctccg ccctcagaat     180
tctccccaga ccactccccg acctgcggcc tcagagagcc cctcagctgc tcccacatgg     240
ccgtgggctg cccagagcca ctgcagcccc accgccacc ctggctcgcg cattgtccta     300
tcgctggatg tccccatcgg cctcttgcag atcttactgg agcaagcccg ggccagggct     360
```

```
gccagggagc aggccaccac caacgcccgc atcctggccc gtgtcggcca ctgctgagcc      420
tgagagaggg ggtcacagtg atagggccac cctggatggg aagacctgga gggcagccac      480
acagctggac ggatgctgcc acatctgggc atacagtgtc tggacgctgc acatctggg       540 catacagtgt ctggacactg ccacatggag ccactgtcat gcaggtcata tcagatctga      600
gtgccccaca gagtcacagt gtgtctggac agcctggaca ttggacattg ctaagttggg      660
tcactgccac atggagtctt gccatgcctg tgtgccccac agacctaata tatgtccgga      720
cagcttggat gctgccacgt aaggtcactg ctgtggcgag tcttgctatg tctgggtgcc      780
ccatagtcac agaacacctg gacaccgcca catgcagtca tcatcatgtt actttcagga      840
gcctcaacac gagagctcaa cactgcctcc gaccagtccc tctgaggccc acaggtctgt      900
catcccatag gccaccacac agagaaatgc tggctgaggg tcacttgctt gctctgtgcc      960
ccatgaggca gcacctgccc cagatggacg gggctgtgag gggtgtctcc aggcacaaag     1020
gcccgaacac aggaagcctg tgaccatggc agccttgtct tatgggcgca tatgtgcgtg     1080
tgtggctgag tctctgacag ctgtgagtgt gtgtgagcag ggtaagggta cgtgaggggt     1140
ctgagaggag tgggtgcttg tcccccaaac ctgcatgaag caagaacaac tcctggccag     1200
gccctgtcct ccccacgtac ccctgcatcc ccagcctcga cccagggaca tgcagggctc     1260
acaggagaca gggctcaggc tgccggagct ccaaccaaac tctgtcccac ttcacgcacg     1320
gactgtcctg ggcaaaggtg ttcacctttc cgagcctcgg tttccttatc tgtaaagcaa     1380
agcgacacca gcaagcctgt gagcattgtg tatatagcag acatggaggt cctgcagcag     1440
gaggtgctca ataaacacaa agcgactgaa ggatgggacc agcaaaaaaa aaaaaaaaa     1500 aaaaaaaaaa aaaaaaaaaa aaaaaaaaaa aaaaaaaaaa aaaaaa                    1546

<210> SEQ ID NO 6
<211> LENGTH: 710
<212> TYPE: DNA
<213> ORGANISM: Homo sapiens

<400> SEQUENCE: 6
caccctgtga tctgtcactt ttatatacac acaggggagg ggaccgtttc catagagagg       60
gaatatcaca gcccacttag gaacaatacc ggagaagcag gagccgagac cccggagcag      120
ccacaagttc atggggacgt gcacggggcc gccctcctgg ccctgaagct gcgccggcct      180
ccctgagcgt ttcgctgcgg agggaagtcc actctcgggg agagatgctg atgccggtcc      240
acttcctgct gctcctgctg ctgctcctgg ggggccccag gacaggcctc cccccacaagt     300 tctacaaagc caagcccatc ttcagctgcc tcaacaccgc cctgtctgag gctgagaagg      360
gccagtggga ggatgcatcc ctgctgagca agaggagctt ccactacctg cgcagcagag      420
acgcctcttc gggagaggag gaggagggca aagagaaaaa gactttcccc atctctgggg      480
ccaggggtgg agccagaggc acccggtaca gatacgtgtc ccaagcacag cccagggaa      540 agccacgcca ggacacggcc aagagtcccc accgcaccaa gttcaccctg tccctcgacg      600
tccccaccaa catcatgaac ctcctcttca acatcgccaa ggccaagaac ctgcgtgccc      660
aggcggccgc caatgcccac ctgatggcgc aaattgggag gaagaagtag                 710

<210> SEQ ID NO 7
<211> LENGTH: 2107
<212> TYPE: DNA
<213> ORGANISM: Homo sapiens

<400> SEQUENCE: 7
```

```
atggacgcgg cactgctcca cagcctgctg gaggccaact gcagcctggc gctggctgaa      60
gagctgctct tggacggctg ggggccaccc ctggaccccg agggtcccta ctcctactgc     120
aacacgacct tggaccagat cggaacgtgc tggccccgca cgcgctgcgg agccctcgtg     180
gagaggccgt gccccgagta cttcaacggc gtcaagtaca cacgacccg gaatgcctat     240
cgagaatgct tggagaatgg gacgtgggcc tcaaagatca actactcaca gtgtgagccc     300
attttggatg acaagcagag gaagtatgac ctgcactacc gcatcgccct tgtcgtcaac     360
tacctgggcc actgcgtatc tgtggcagcc ctggtggccg ccttcctgct tttcctggcc     420
ctgcggagca ttcgctgtct gcggaatgtg attcactgga acctcatcac caccttatc      480
ctgcgaaatg tcatgtggtt cctgctgcag ctcgttgacc atgaagtgca cgagagcaat     540
gaggtctggt gccgctgcat caccaccatc ttcaactact cgtggtgac caacttcttc      600
tggatgtttg tggaaggctg ctacctgcac acggccattg tcatgaccta ctccactgag     660
cgcctgcgca agtgcctctt cctcttcatc ggatggtgca tccccttccc catcatcgtc     720
gcctgggcca tcgcaagct ctactatgag aatgaacagt gctggtttgg caaggagcct      780
ggcgacctgg tggactacat ctaccaaggc cccatcattc tcgtgctcct gatcaatttc     840
gtatttctgt tcaacatcgt caggatccta atgacaaagt acgcgcgtc caccacatcc      900
gagacaatcc agtacaggaa ggcagtgaag gccaccctgg tgctcctgcc cctcctgggc     960
atcacctaca tgctcttctt cgtcaatccc ggggaggacg acctgtcaca gatcatgttc    1020
atctatttca ctccttcct gcagtcgttc cagggtttct tcgtgtctgt cttctactgc     1080
ttcttcaatg gagaggtgcg ctcagccgtg aggaagaggt ggcaccgctg gcaggaccat    1140
cactcccttc gagtccccat ggcccgggcc atgtccatcc ctacatcacc cacacggatc    1200
agcttccaca gcatcaagca gacggccgct gtgtgacccc tcggtcgccc acctgcacag    1260
ctcccctgtc ctcctccacc ttcttcctct gggttctctg tgctgggcag gctctcgtgg    1320
ggcaggagat gggagggag agaccagctc tccagcctgg caggaaagag ggggtgcggc    1380
agccaagggg gactgcaagg gacagggatg agtgggggcc accaggctca gcgcaagagg    1440
aagcagaggg aattcacagg acccctgag aagagccagt cagatgtctg caggcatttg     1500
cccatcccag cctctctggc cagggcctta ctgggcccag agcagagaag gacctgtcca    1560
acacacacag ctatttatag tagcagacac agggctcccc tgccctactc atggagccag    1620
cagccaggca atggtgtggc cctgcactgg cccttggact ccacactcag tggtgccctg    1680
cagttgggtg ggttacgcca gcaaaggatc agtttggctg ccttatccca gggctgtcac    1740
ctagagaggc tcacttgtac cccacccctgt tcctgtgtcc cctccccagc catcctcccg    1800
ccttgggggc tccatgaagg atgcaggctt ccaggcctgg cttcctctct gggagaccc     1860
cttctctgcc tagtccacag attaggcaat caaggaagac gccatcaggg aagccacatc    1920
cttagtcaac cagttgcatc gtgcggggca aaatgaggag cagaggcatg gaggagggag    1980
gcgtgggatg ggaatagcag aaccaccatg tcttcagtga ttgaaactca tacccccattg   2040
cccttttgccc tccagtctcc ccttcagaaa catctctgct ctctgtgaaa taaaccatgc    2100
ctcttgg                                                              2107
```

<210> SEQ ID NO 8
<211> LENGTH: 411
<212> TYPE: PRT
<213> ORGANISM: Homo sapiens

<400> SEQUENCE: 8

```
Met Asp Ala Ala Leu Leu His Ser Leu Leu Glu Ala Asn Cys Ser Leu
1               5                   10                  15
Ala Leu Ala Glu Glu Leu Leu Leu Asp Gly Trp Gly Pro Pro Leu Asp
            20                  25                  30
Pro Glu Gly Pro Tyr Ser Tyr Cys Asn Thr Thr Leu Asp Gln Ile Gly
        35                  40                  45
Thr Cys Trp Pro Arg Ser Ala Ala Gly Ala Leu Val Glu Arg Pro Cys
50                  55                  60
Pro Glu Tyr Phe Asn Gly Val Lys Tyr Asn Thr Thr Arg Asn Ala Tyr
65                  70                  75                  80
Arg Glu Cys Leu Glu Asn Gly Thr Trp Ala Ser Lys Ile Asn Tyr Ser
                85                  90                  95
Gln Cys Glu Pro Ile Leu Asp Asp Lys Gln Arg Lys Tyr Asp Leu His
            100                 105                 110
Tyr Arg Ile Ala Leu Val Val Asn Tyr Leu Gly His Cys Val Ser Val
        115                 120                 125
Ala Ala Leu Val Ala Ala Phe Leu Leu Phe Leu Ala Leu Arg Ser Ile
130                 135                 140
Arg Cys Leu Arg Asn Val Ile His Trp Asn Leu Ile Thr Thr Phe Ile
145                 150                 155                 160
Leu Arg Asn Val Met Trp Phe Leu Leu Gln Leu Val Asp His Glu Val
                165                 170                 175
His Glu Ser Asn Glu Val Trp Cys Arg Cys Ile Thr Thr Ile Phe Asn
            180                 185                 190
Tyr Phe Val Val Thr Asn Phe Phe Trp Met Phe Val Glu Gly Cys Tyr
        195                 200                 205
Leu His Thr Ala Ile Val Met Thr Tyr Ser Thr Glu Arg Leu Arg Lys
210                 215                 220
Cys Leu Phe Leu Phe Ile Gly Trp Cys Ile Pro Phe Pro Ile Ile Val
225                 230                 235                 240
Ala Trp Ala Ile Gly Lys Leu Tyr Tyr Glu Asn Glu Gln Cys Trp Phe
                245                 250                 255
Gly Lys Glu Pro Gly Asp Leu Val Asp Tyr Ile Tyr Gln Gly Pro Ile
            260                 265                 270
Ile Leu Val Leu Leu Ile Asn Phe Val Phe Leu Phe Asn Ile Val Arg
        275                 280                 285
Ile Leu Met Thr Lys Leu Arg Ala Ser Thr Thr Ser Glu Thr Ile Gln
290                 295                 300
Tyr Arg Lys Ala Val Lys Ala Thr Leu Val Leu Leu Pro Leu Leu Gly
305                 310                 315                 320
Ile Thr Tyr Met Leu Phe Phe Val Asn Pro Gly Glu Asp Asp Leu Ser
                325                 330                 335
Gln Ile Met Phe Ile Tyr Phe Asn Ser Phe Leu Gln Ser Phe Gln Gly
            340                 345                 350
Phe Phe Val Ser Val Phe Tyr Cys Phe Phe Asn Gly Glu Val Arg Ser
        355                 360                 365
Ala Val Arg Lys Arg Trp His Arg Trp Gln Asp His His Ser Leu Arg
370                 375                 380
Val Pro Met Ala Arg Ala Met Ser Ile Pro Thr Ser Pro Thr Arg Ile
385                 390                 395                 400
Ser Phe His Ser Ile Lys Gln Thr Ala Ala Val
                405                 410
```

```
<210> SEQ ID NO 9
<211> LENGTH: 40
<212> TYPE: PRT
<213> ORGANISM: Phyllomedusa sauvagei

<400> SEQUENCE: 9

Glu Gly Pro Pro Ile Ser Ile Asp Leu Ser Leu Glu Leu Leu Arg Lys
1               5                   10                  15

Met Ile Glu Ile Glu Lys Gln Glu Lys Glu Lys Gln Gln Ala Ala Asn
                20                  25                  30

Asn Arg Leu Leu Leu Asp Thr Ile
            35                  40

<210> SEQ ID NO 10
<211> LENGTH: 30
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (1)..(1)
<223> OTHER INFORMATION: Xaa = DPhe
<220> FEATURE:
<221> NAME/KEY: Xaa
<222> LOCATION: (3)..(3)
<223> OTHER INFORMATION: Xaa = C(alpha)MeLeu
<220> FEATURE:
<221> NAME/KEY: Xaa
<222> LOCATION: (7)..(7)
<223> OTHER INFORMATION: Xaa = Nle
<220> FEATURE:
<221> NAME/KEY: Xaa
<222> LOCATION: (21)..(21)
<223> OTHER INFORMATION: Xaa = Glu linked to Lys(24) via a lactam
      bridge.
<220> FEATURE:
<221> NAME/KEY: Xaa
<222> LOCATION: (24)..(24)
<223> OTHER INFORMATION: Xaa = Lys linked to Glu(21) via a lactam
      bridge.
<220> FEATURE:
<221> NAME/KEY: Xaa
<222> LOCATION: (29)..(29)
<223> OTHER INFORMATION: Xaa = C(alpha)MeLeu

<400> SEQUENCE: 10

Xaa His Xaa Leu Arg Lys Xaa Ile Glu Ile Glu Lys Gln Glu Lys Glu
1               5                   10                  15

Lys Gln Gln Ala Xaa Asn Asn Xaa Leu Leu Leu Asp Xaa Ile
                20                  25                  30

<210> SEQ ID NO 11
<211> LENGTH: 30
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: Xaa
<222> LOCATION: (11)..(11)
<223> OTHER INFORMATION: Xaa = DPhe

<400> SEQUENCE: 11

Xaa His Leu Leu Arg Lys Met Ile Glu Ile Glu Lys Gln Glu Lys Glu
```

```
                1               5                   10                  15
Lys Gln Gln Ala Ala Asn Asn Arg Leu Leu Leu Asp Thr Ile
            20                  25                  30

<210> SEQ ID NO 12
<211> LENGTH: 41
<212> TYPE: PRT
<213> ORGANISM: Homo sapiens

<400> SEQUENCE: 12

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

<210> SEQ ID NO 13
<211> LENGTH: 30
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (1)..(1)
<223> OTHER INFORMATION: Xaa = DPhe
<220> FEATURE:
<221> NAME/KEY: Xaa
<222> LOCATION: (3)..(3)
<223> OTHER INFORMATION: Xaa = Leu or C(alpha)MeLeu
<220> FEATURE:
<221> NAME/KEY: Xaa
<222> LOCATION: (6)..(6)
<223> OTHER INFORMATION: Xaa = Lys or Glu
<220> FEATURE:
<221> NAME/KEY: Xaa
<222> LOCATION: (7)..(7)
<223> OTHER INFORMATION: Xaa = Met, Nle or Val
<220> FEATURE:
<221> NAME/KEY: Xaa
<222> LOCATION: (8)..(8)
<223> OTHER INFORMATION: Xaa = Ile or Leu
<220> FEATURE:
<221> NAME/KEY: Xaa
<222> LOCATION: (10)..(10)
<223> OTHER INFORMATION: Xaa = Ile or Nle
<220> FEATURE:
<221> NAME/KEY: Xaa
<222> LOCATION: (11)..(11)
<223> OTHER INFORMATION: Xaa = Ala or Glu
<220> FEATURE:
<221> NAME/KEY: Xaa
<222> LOCATION: (12)..(12)
<223> OTHER INFORMATION: Xaa = Lys or Arg
<220> FEATURE:
<221> NAME/KEY: Xaa
<222> LOCATION: (13)..(13)
<223> OTHER INFORMATION: Xaa = Gln or Ala
<220> FEATURE:
<221> NAME/KEY: Xaa
<222> LOCATION: (15)..(15)
<223> OTHER INFORMATION: Xaa = Gln or Lys
<220> FEATURE:
<221> NAME/KEY: Xaa
<222> LOCATION: (16)..(16)
<223> OTHER INFORMATION: Xaa = Glu or Leu
<220> FEATURE:
<221> NAME/KEY: Xaa
<222> LOCATION: (17)..(17)
<223> OTHER INFORMATION: Xaa = Lys or Ala
<220> FEATURE:
<221> NAME/KEY: Xaa
```

```
<222> LOCATION: (21)..(21)
<223> OTHER INFORMATION: Xaa = Ala, Gln, Glu or Glu linked to Lys(24)
      via a lactam bridge.
<220> FEATURE:
<221> NAME/KEY: Xaa
<222> LOCATION: (22)..(22)
<223> OTHER INFORMATION: Xaa = Asn or Ser
<220> FEATURE:
<221> NAME/KEY: Xaa
<222> LOCATION: (24)..(24)
<223> OTHER INFORMATION: Xaa = Arg, Lys(Ac), Lys, Lys linked to Glu(21)
      via a lactam bridge or Glu linked to Lys(27) via a lactam bridge.
<220> FEATURE:
<221> NAME/KEY: Xaa
<222> LOCATION: (25)..(25)
<223> OTHER INFORMATION: Xaa = Leu or Lys
<220> FEATURE:
<221> NAME/KEY: Xaa
<222> LOCATION: (27)..(27)
<223> OTHER INFORMATION: Xaa = Leu, Nle or Lys linked to Glu(24) via a
      lactam bridge.
<220> FEATURE:
<221> NAME/KEY: Xaa
<222> LOCATION: (28)..(28)
<223> OTHER INFORMATION: Xaa = Asp or Glu
<220> FEATURE:
<221> NAME/KEY: Xaa
<222> LOCATION: (29)..(29)
<223> OTHER INFORMATION: Xaa = Thr, Ile or C(alpha)Leu

<400> SEQUENCE: 13

Xaa His Xaa Leu Arg Xaa Xaa Xaa Glu Xaa Xaa Xaa Xaa Glu Xaa Xaa
1               5                   10                  15

Xaa Gln Gln Ala Xaa Xaa Asn Xaa Xaa Leu Xaa Xaa Xaa Ile
            20                  25                  30

<210> SEQ ID NO 14
<211> LENGTH: 30
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (1)..(1)
<223> OTHER INFORMATION: Xaa = DPhe
<220> FEATURE:
<221> NAME/KEY: Xaa
<222> LOCATION: (10)..(10)
<223> OTHER INFORMATION: Xaa = Nle
<220> FEATURE:
<221> NAME/KEY: Xaa
<222> LOCATION: (21)..(21)
<223> OTHER INFORMATION: Xaa = Glu linked to Lys(24) via a lactam
      bridge.
<220> FEATURE:
<221> NAME/KEY: Xaa
<222> LOCATION: (24)..(24)
<223> OTHER INFORMATION: Xaa = Lys linked to Glu(21) via a lactam
      bridge.
<220> FEATURE:
<221> NAME/KEY: Xaa
<222> LOCATION: (27)..(27)
<223> OTHER INFORMATION: Xaa = Nle

<400> SEQUENCE: 14

Xaa His Leu Leu Arg Glu Val Leu Glu Xaa Ala Arg Ala Glu Gln Leu
1               5                   10                  15

Ala Gln Gln Ala Xaa Ser Asn Xaa Lys Leu Xaa Glu Ile Ile
            20                  25                  30

<210> SEQ ID NO 15
<211> LENGTH: 33
```

```
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa = DPhe
<220> FEATURE:
<221> NAME/KEY: Xaa
<222> LOCATION: (6)..(6)
<223> OTHER INFORMATION: Xaa = C(alpha)MeLeu
<220> FEATURE:
<221> NAME/KEY: Xaa
<222> LOCATION: (10)..(10)
<223> OTHER INFORMATION: Xaa = Nle
<220> FEATURE:
<221> NAME/KEY: Xaa
<222> LOCATION: (24)..(24)
<223> OTHER INFORMATION: Xaa = Glu linked to Lys(27) via a lactam
      bridge.
<220> FEATURE:
<221> NAME/KEY: Xaa
<222> LOCATION: (27)..(27)
<223> OTHER INFORMATION: Xaa = Lys linked to Glu(24) via a lactam
      bridge.
<220> FEATURE:
<221> NAME/KEY: Xaa
<222> LOCATION: (32)..(32)
<223> OTHER INFORMATION: Xaa = C(alpha)MeLeu

<400> SEQUENCE: 15

Asp Leu Ser Xaa His Xaa Leu Arg Lys Xaa Ile Glu Ile Glu Lys Gln
1               5                   10                  15

Glu Lys Glu Lys Gln Gln Ala Xaa Asn Asn Xaa Leu Leu Leu Asp Xaa
            20                  25                  30

Ile

<210> SEQ ID NO 16
<211> LENGTH: 33
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa = DPhe
<220> FEATURE:
<221> NAME/KEY: Xaa
<222> LOCATION: (6)..(6)
<223> OTHER INFORMATION: Xaa = C(alpha)MeLeu
<220> FEATURE:
<221> NAME/KEY: Xaa
<222> LOCATION: (10)..(10)
<223> OTHER INFORMATION: Xaa = Nle
<220> FEATURE:
<221> NAME/KEY: Xaa
<222> LOCATION: (32)..(32)
<223> OTHER INFORMATION: Xaa = C(alpha)MeLeu

<400> SEQUENCE: 16

Asp Leu Ser Xaa His Xaa Leu Arg Lys Xaa Ile Glu Ile Glu Lys Gln
1               5                   10                  15

Glu Lys Glu Lys Gln Gln Ala Glu Asn Asn Lys Leu Leu Leu Asp Xaa
            20                  25                  30

Ile

<210> SEQ ID NO 17
<211> LENGTH: 33
<212> TYPE: PRT
```

```
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa = DPhe
<220> FEATURE:
<221> NAME/KEY: Xaa
<222> LOCATION: (6)..(6)
<223> OTHER INFORMATION: Xaa = C(alpha)MeLeu
<220> FEATURE:
<221> NAME/KEY: Xaa
<222> LOCATION: (10)..(10)
<223> OTHER INFORMATION: Xaa = Nle
<220> FEATURE:
<221> NAME/KEY: Xaa
<222> LOCATION: (27)..(27)
<223> OTHER INFORMATION: Xaa = Lys(Ac)
<220> FEATURE:
<221> NAME/KEY: Xaa
<222> LOCATION: (32)..(32)
<223> OTHER INFORMATION: Xaa = C(alpha)MeLeu

<400> SEQUENCE: 17

Asp Leu Ser Xaa His Xaa Leu Arg Lys Xaa Ile Glu Ile Glu Lys Gln
1               5                   10                  15

Glu Lys Glu Lys Gln Gln Ala Gln Asn Asn Xaa Leu Leu Leu Asp Xaa
            20                  25                  30

Ile

<210> SEQ ID NO 18
<211> LENGTH: 33
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa = DPhe
<220> FEATURE:
<221> NAME/KEY: Xaa
<222> LOCATION: (6)..(6)
<223> OTHER INFORMATION: Xaa = C(alpha)MeLeu
<220> FEATURE:
<221> NAME/KEY: Xaa
<222> LOCATION: (10)..(10)
<223> OTHER INFORMATION: Xaa = Nle
<220> FEATURE:
<221> NAME/KEY: Xaa
<222> LOCATION: (27)..(27)
<223> OTHER INFORMATION: Xaa = Glu linked to Lys(30) via a lactam
      bridge.
<220> FEATURE:
<221> NAME/KEY: Xaa
<222> LOCATION: (30)..(30)
<223> OTHER INFORMATION: Xaa = Lys linked to Glu(27) via a lactam
      bridge.
<220> FEATURE:
<221> NAME/KEY: Xaa
<222> LOCATION: (32)..(32)
<223> OTHER INFORMATION: Xaa = C(alpha)MeLeu

<400> SEQUENCE: 18

Asp Leu Ser Xaa His Xaa Leu Arg Lys Xaa Ile Glu Ile Glu Lys Gln
1               5                   10                  15

Glu Lys Glu Lys Gln Gln Ala Ala Asn Asn Xaa Leu Leu Xaa Asp Xaa
            20                  25                  30

Ile
```

```
<210> SEQ ID NO 19
<211> LENGTH: 30
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa = DPhe
<220> FEATURE:
<221> NAME/KEY: Xaa
<222> LOCATION: (3)..(3)
<223> OTHER INFORMATION: Xaa = C(alpha)MeLeu
<220> FEATURE:
<221> NAME/KEY: Xaa
<222> LOCATION: (7)..(7)
<223> OTHER INFORMATION: Xaa = Nle
<220> FEATURE:
<221> NAME/KEY: Xaa
<222> LOCATION: (24)..(24)
<223> OTHER INFORMATION: Xaa = Lys(Ac)
<220> FEATURE:
<221> NAME/KEY: Xaa
<222> LOCATION: (29)..(29)
<223> OTHER INFORMATION: Xaa = C(alpha)MeLeu

<400> SEQUENCE: 19

Xaa His Xaa Leu Arg Lys Xaa Ile Glu Ile Glu Lys Gln Glu Lys Glu
1               5                   10                  15

Lys Gln Gln Ala Gln Asn Asn Xaa Leu Leu Leu Asp Xaa Ile
            20                  25                  30

<210> SEQ ID NO 20
<211> LENGTH: 40
<212> TYPE: PRT
<213> ORGANISM: Homo sapiens

<400> SEQUENCE: 20

Asp Asn Pro Ser Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
            35                  40

<210> SEQ ID NO 21
<211> LENGTH: 40
<212> TYPE: PRT
<213> ORGANISM: Mus musculus

<400> SEQUENCE: 21

Asp Asp Pro Pro Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
            35                  40

<210> SEQ ID NO 22
<211> LENGTH: 1558
<212> TYPE: DNA
<213> ORGANISM: Homo sapiens

<400> SEQUENCE: 22
ctgtgctcaa gcaatctgcc taccttggct tccccaagtg ctgagattat gggtgtgagc    60
```

```
cactgcacct ggccaagaat ccgaatggat tcaaagatac cttgaaataa ttcctcaatg     120
caacacacac acatatgcca gggttggtca aatgggaaga gagccttggc ctgaagacag     180
ggacctgggc tttcctcagc tcttctgcca aggtccctac tcctactgca acacgacctt     240
ggaccagatc ggaacgtgct ggccccgcag cgctgccgga ccctcgtgg agaggccgtg      300 ccccgagtac ttcaacggcg tcaagtacaa cacgacccgg aatgcctatc gagaatgctt     360
ggagaatggg acgtgggcct caaagatcaa ctactcacag tgtgagccca ttttggatga     420
caagcagagg aagtatgacc tgcactaccg catcgccctt gtcgtcaact acctgggcca     480
ctgcgtatct gtggcagccc tggtggccgc cttcctgctt ttcctggccc tgcggagcat     540
tcgctgtctg cggaatgtga ttcactggaa cctcatcacc accttttatcc tgcgaaatgt    600 catgtggttc ctgctgcagc tcgttgacca tgaagtgcac gagagcaatg aggtctggtg     660
ccgctgcatc accaccatct tcaactactt cgtggtgacc aacttcttct ggatgttttgt    720 ggaaggctgc tacctgcaca cggccattgt catgacctac tccactgagc gcctgcgcaa     780
gtgcctcttc ctcttcatcg gatggtgcat ccccttcccc atcatcgtcg cctgggccat     840
cggcaagctc tactatgaga atgaacagtg ctggtttggc aaggagcctg gcgacctggt     900
ggactacatc taccaaggcc ccatcattct cgtgctcctg atcaatttcg tatttctgtt     960
caacatcgtc aggatcctaa tgacaaagtt acgcgcgtcc accacatccg agacaatcca    1020
gtacaggaag gcagtgaagg ccaccctggt gctcctgccc ctcctgggca tcacctacat    1080
gctcttcttc gtcaatcccg gggaggacga cctgtcacag atcatgttca tctatttcaa    1140
ctccttcctg cagtcgttcc agggtttctt cgtgtctgtc ttctactgct tcttcaatgg    1200
agaggtgcgc tcagccgtga ggaagaggtg gcaccgctgg caggaccatc actcccttcg    1260
agtccccatg gcccgggcca tgtccatccc tacatcaccc acacggatca gcttccacag    1320
catcaagcag acggccgctg tgtgaccccct cggtcgccca cctgcacagc tcccctgtcc    1380
tcctccacct tcttcctctg ggttctctgt gctgggcagg ctctcgtggg gcaggagatg    1440
ggaggggaga gaccagctct ccagcctggc aggaaagagg gggtgcggca gccaagggg     1500 actgcaaggg acagggatga gtggggccca ccaggctcag cgcaagagga agcagagg      1558
```

<210> SEQ ID NO 23
<211> LENGTH: 397
<212> TYPE: PRT
<213> ORGANISM: Homo sapiens

<400> SEQUENCE: 23

```
Met Gly Arg Glu Pro Trp Pro Glu Asp Arg Asp Leu Gly Phe Pro Gln
1               5                   10                  15

Leu Phe Cys Gln Gly Pro Tyr Ser Tyr Cys Asn Thr Thr Leu Asp Gln
            20                  25                  30

Ile Gly Thr Cys Trp Pro Arg Ser Ala Ala Gly Ala Leu Val Glu Arg
        35                  40                  45

Pro Cys Pro Glu Tyr Phe Asn Gly Val Lys Tyr Asn Thr Thr Arg Asn
    50                  55                  60

Ala Tyr Arg Glu Cys Leu Glu Asn Gly Thr Trp Ala Ser Lys Ile Asn
65                  70                  75                  80

Tyr Ser Gln Cys Glu Pro Ile Leu Asp Asp Lys Gln Arg Lys Tyr Asp
                85                  90                  95

Leu His Tyr Arg Ile Ala Leu Val Val Asn Tyr Leu Gly His Cys Val
            100                 105                 110
```

```
Ser Val Ala Ala Leu Val Ala Ala Phe Leu Leu Phe Leu Ala Leu Arg
    115                 120                 125
Ser Ile Arg Cys Leu Arg Asn Val Ile His Trp Asn Leu Ile Thr Thr
130                 135                 140
Phe Ile Leu Arg Asn Val Met Trp Phe Leu Leu Gln Leu Val Asp His
145                 150                 155                 160
Glu Val His Glu Ser Asn Glu Val Trp Cys Arg Cys Ile Thr Thr Ile
                165                 170                 175
Phe Asn Tyr Phe Val Val Thr Asn Phe Phe Trp Met Phe Val Glu Gly
            180                 185                 190
Cys Tyr Leu His Thr Ala Ile Val Met Thr Tyr Ser Thr Glu Arg Leu
        195                 200                 205
Arg Lys Cys Leu Phe Leu Phe Ile Gly Trp Cys Ile Pro Phe Pro Ile
    210                 215                 220
Ile Val Ala Trp Ala Ile Gly Lys Leu Tyr Tyr Glu Asn Glu Gln Cys
225                 230                 235                 240
Trp Phe Gly Lys Glu Pro Gly Asp Leu Val Asp Tyr Ile Tyr Gln Gly
                245                 250                 255
Pro Ile Ile Leu Val Leu Leu Ile Asn Phe Val Phe Leu Phe Asn Ile
            260                 265                 270
Val Arg Ile Leu Met Thr Lys Leu Arg Ala Ser Thr Thr Ser Glu Thr
        275                 280                 285
Ile Gln Tyr Arg Lys Ala Val Lys Ala Thr Leu Val Leu Leu Pro Leu
    290                 295                 300
Leu Gly Ile Thr Tyr Met Leu Phe Phe Val Asn Pro Gly Glu Asp Asp
305                 310                 315                 320
Leu Ser Gln Ile Met Phe Ile Tyr Phe Asn Ser Phe Leu Gln Ser Phe
                325                 330                 335
Gln Gly Phe Phe Val Ser Val Phe Tyr Cys Phe Phe Asn Gly Glu Val
            340                 345                 350
Arg Ser Ala Val Arg Lys Arg Trp His Arg Trp Gln Asp His His Ser
        355                 360                 365
Leu Arg Val Pro Met Ala Arg Ala Met Ser Ile Pro Thr Ser Pro Thr
    370                 375                 380
Arg Ile Ser Phe His Ser Ile Lys Gln Thr Ala Ala Val
385                 390                 395

<210> SEQ ID NO 24
<211> LENGTH: 1600
<212> TYPE: DNA
<213> ORGANISM: Homo sapiens

<400> SEQUENCE: 24
ggggctggcc agggtgtgac caccgtgctg ggcagcaggc tccagtccct aaccccagc       60 cactactggc atgaggggtc cctcagggcc cccaggcctc ctctacgtcc acacctcct     120 cctctgcctg ctctgcctcc tcccaccgcc gctccaatac gcagccgggc agagccagat    180
gcccaaagac cagcccctgt gggcacttct ggagcagtac tgccacacca tcatgaccct    240
caccaacctc tcaggtccct actcctactg caacacgacc ttggaccaga tcggaacgtg    300
ctggccccgc agcgctgccg gagccctcgt ggagaggccg tgccccgagt acttcaacgg    360
cgtcaagtac aacacgaccc ggaatgccta tcgagaatgc ttggagaatg ggacgtggc    420 ctcaaagatc aactactcac agtgtgagcc cattttggat gacaagcaga ggaagtatga    480
cctgcactac cgcatcgccc ttgtcgtcaa ctacctgggc cactgcgtat ctgtggcagc    540
```

-continued

```
cctggtggcc gccttcctgc ttttcctggc cctgcggagc attcgctgtc tgcggaatgt   600
gattcactgg aacctcatca ccacctttat cctgcgaaat gtcatgtggt tcctgctgca   660
gctcgttgac catgaagtgc acgagagcaa tgaggtctgg tgccgctgca tcaccaccat   720
cttcaactac ttcgtggtga ccaacttctt ctggatgttt gtggaaggct gctacctgca   780
cacggccatt gtcatgacct actccactga gcgcctgcgc aagtgcctct tcctcttcat   840
cggatggtgc atccccttcc ccatcatcgt cgcctgggcc atcggcaagc tctactatga   900
gaatgaacag tgctggtttg caaggagcc tggcgacctg gtggactaca tctaccaagg   960
ccccatcatt ctcgtgctcc tgatcaattt cgtatttctg ttcaacatcg tcaggatcct  1020
aatgacaaag ttacgcgcgt ccaccacatc cgagacaatc cagtacagga aggcagtgaa  1080
ggccacctg gtgctcctgc ccctcctggg catcacctac atgctcttct tcgtcaatcc  1140
cggggaggac gacctgtcac agatcatgtt catctatttc aactcctcc tgcagtcgtt  1200
ccagggtttc ttcgtgtctg tcttctactg cttcttcaat ggagaggtgc gctcagccgt  1260
gaggaagagg tggcaccgct ggcaggacca tcactccctt cgagtcccca tggcccgggc  1320
catgtccatc cctacatcac ccacacggat cagcttccac agcatcaagc agacggccgc  1380
tgtgtgaccc ctcggtcgcc cacctgcaca gctcccctgt cctcctccac cttcttcctc  1440
tgggttctct gtgctgggca ggctctcgtg gggcaggaga tggaggggga gagaccagct  1500
ctccagcctg gcaggaaaga gggggtgcgg cagccaaggg ggactgcaag ggacagggat  1560
gagtgggggc caccaggctc agcgcaagag gaagcagagg                       1600
```

<210> SEQ ID NO 25
<211> LENGTH: 438
<212> TYPE: PRT
<213> ORGANISM: Homo sapiens

<400> SEQUENCE: 25

```
Met Arg Gly Pro Ser Gly Pro Pro Gly Leu Leu Tyr Val Pro His Leu
1               5                   10                  15

Leu Leu Cys Leu Leu Cys Leu Leu Pro Pro Leu Gln Tyr Ala Ala
            20                  25                  30

Gly Gln Ser Gln Met Pro Lys Asp Gln Pro Leu Trp Ala Leu Leu Glu
        35                  40                  45

Gln Tyr Cys His Thr Ile Met Thr Leu Thr Asn Leu Ser Gly Pro Tyr
    50                  55                  60

Ser Tyr Cys Asn Thr Thr Leu Asp Gln Ile Gly Thr Cys Trp Pro Arg
65                  70                  75                  80

Ser Ala Ala Gly Ala Leu Val Glu Arg Pro Cys Pro Glu Tyr Phe Asn
                85                  90                  95

Gly Val Lys Tyr Asn Thr Thr Arg Asn Ala Tyr Arg Glu Cys Leu Glu
            100                 105                 110

Asn Gly Thr Trp Ala Ser Lys Ile Asn Tyr Ser Gln Cys Glu Pro Ile
        115                 120                 125

Leu Asp Asp Lys Gln Arg Lys Tyr Asp Leu His Tyr Arg Ile Ala Leu
    130                 135                 140

Val Val Asn Tyr Leu Gly His Cys Val Ser Val Ala Ala Leu Val Ala
145                 150                 155                 160

Ala Phe Leu Leu Phe Leu Ala Leu Arg Ser Ile Arg Cys Leu Arg Asn
                165                 170                 175

Val Ile His Trp Asn Leu Ile Thr Thr Phe Ile Leu Arg Asn Val Met
```

-continued

```
                180                 185                 190
Trp Phe Leu Leu Gln Leu Val Asp His Glu Val His Glu Ser Asn Glu
            195                 200                 205

Val Trp Cys Arg Cys Ile Thr Thr Ile Phe Asn Tyr Phe Val Val Thr
        210                 215                 220

Asn Phe Phe Trp Met Phe Val Glu Gly Cys Tyr Leu His Thr Ala Ile
225                 230                 235                 240

Val Met Thr Tyr Ser Thr Glu Arg Leu Arg Lys Cys Leu Phe Leu Phe
                245                 250                 255

Ile Gly Trp Cys Ile Pro Phe Pro Ile Ile Val Ala Trp Ala Ile Gly
            260                 265                 270

Lys Leu Tyr Tyr Glu Asn Glu Gln Cys Trp Phe Gly Lys Glu Pro Gly
        275                 280                 285

Asp Leu Val Asp Tyr Ile Tyr Gln Gly Pro Ile Ile Leu Val Leu Leu
    290                 295                 300

Ile Asn Phe Val Phe Leu Phe Asn Ile Val Arg Ile Leu Met Thr Lys
305                 310                 315                 320

Leu Arg Ala Ser Thr Thr Ser Glu Thr Ile Gln Tyr Arg Lys Ala Val
                325                 330                 335

Lys Ala Thr Leu Val Leu Leu Pro Leu Leu Gly Ile Thr Tyr Met Leu
            340                 345                 350

Phe Phe Val Asn Pro Gly Glu Asp Asp Leu Ser Gln Ile Met Phe Ile
        355                 360                 365

Tyr Phe Asn Ser Phe Leu Gln Ser Phe Gln Gly Phe Phe Val Ser Val
    370                 375                 380

Phe Tyr Cys Phe Phe Asn Gly Glu Val Arg Ser Ala Val Arg Lys Arg
385                 390                 395                 400

Trp His Arg Trp Gln Asp His His Ser Leu Arg Val Pro Met Ala Arg
                405                 410                 415

Ala Met Ser Ile Pro Thr Ser Pro Thr Arg Ile Ser Phe His Ser Ile
            420                 425                 430

Lys Gln Thr Ala Ala Val
        435

<210> SEQ ID NO 26
<211> LENGTH: 36
<212> TYPE: PRT
<213> ORGANISM: Homo sapiens

<400> SEQUENCE: 26

Met Asp Ala Ala Leu Leu His Ser Leu Leu Glu Ala Asn Cys Ser Leu
1               5                   10                  15

Ala Leu Ala Glu Glu Leu Leu Leu Asp Gly Trp Gly Pro Pro Leu Asp
                20                  25                  30

Pro Glu Gly Pro
        35

<210> SEQ ID NO 27
<211> LENGTH: 63
<212> TYPE: PRT
<213> ORGANISM: Homo sapiens

<400> SEQUENCE: 27

Met Arg Gly Pro Ser Gly Pro Gly Leu Leu Tyr Val Pro His Leu
1               5                   10                  15

Leu Leu Cys Leu Leu Cys Leu Leu Pro Pro Pro Leu Gln Tyr Ala Ala
```

```
                    20                  25                  30
Gly Gln Ser Gln Met Pro Lys Asp Gln Pro Leu Trp Ala Leu Leu Glu
            35                  40                  45

Gln Tyr Cys His Thr Ile Met Thr Leu Thr Asn Leu Ser Gly Pro
    50                  55                  60

<210> SEQ ID NO 28
<211> LENGTH: 22
<212> TYPE: PRT
<213> ORGANISM: Homo sapiens

<400> SEQUENCE: 28

Met Gly Arg Glu Pro Trp Pro Glu Asp Arg Asp Leu Gly Phe Pro Gln
1               5                   10                  15

Leu Phe Cys Gln Gly Pro
            20

<210> SEQ ID NO 29
<211> LENGTH: 102
<212> TYPE: DNA
<213> ORGANISM: Homo sapiens

<400> SEQUENCE: 29
atggacgcgg cactgctcca cagcctgctg gaggccaact gcagcctggc gctggctgaa      60
gagctgctct tggacggctg ggggccaccc ctggaccccg ag                       102

<210> SEQ ID NO 30
<211> LENGTH: 254
<212> TYPE: DNA
<213> ORGANISM: Homo sapiens

<400> SEQUENCE: 30
ggggctggcc agggtgtgac caccgtgctg ggcagcaggc tccagtccct aaccccccagc     60 cactactggc atgaggggtc cctcagggcc ccaggcctc ctctacgtcc cacacctcct     120
cctctgcctg ctctgcctcc tcccaccgcc gctccaatac gcagccgggc agagccagat    180
gcccaaagac cagcccctgt gggcacttct ggagcagtac tgccacacca tcatgaccct    240
caccaacctc tcag                                                      254

<210> SEQ ID NO 31
<211> LENGTH: 212
<212> TYPE: DNA
<213> ORGANISM: Homo sapiens

<400> SEQUENCE: 31
ctgtgctcaa gcaatctgcc taccttggct tccccaagtg ctgagattat gggtgtgagc      60
cactgcacct ggccaagaat ccgaatggat tcaaagatac cttgaaataa ttcctcaatg    120
caacacacac acatatgcca gggttggtca aatgggaaga gagccttggc ctgaagacag    180
ggacctgggc tttcctcagc tcttctgcca ag                                  212
```

METHODS OF INCREASING INSULIN SENSITIVITY OR DECREASING INSULIN SECRETION BY ADMINISTERING CORTICOTROPIN RELEASING FACTOR RECEPTOR-2 INHIBITORS

This application claims priority to U.S. Provisional Patent application Ser. No. 60/762,906 filed Jan. 27, 2006, which is incorporated by reference in its entirety.

The government may own certain right in relation to the present invention pursuant to National Institute of Diabetes and Digestive and Kidney Diseases (NIDDK) grant number DK 26741 from the National Institutes of Health.

BACKGROUND OF THE INVENTION

1. Field of the Invention

The present invention general concerns the endocrinology, more specifically methods for maintaining blood sugar homeostasis.

2. Description of Related Art

Regulation of glucose homeostasis in the bloodstream must be tightly controlled to maintain healthy metabolic function. Low serum glucose levels (hypoglycemia) can lead to weakness, headaches, confusion and if unchecked ultimately convulsions, coma and death. On the other hand, hyperglycemia causes excess urine production, thirst, weight loss, fatigue, and in sever cases can also result in coma and death. Chronically high blood sugar also can result in long term tissue damage that may contribute to diabetic complications such as blindness, kidney failure, impotence, atherosclerosis, and increased vulnerability to infection.

In a healthy subject pancreatic tissue is responsible for secretion of hormones that regulate serum glucose homeostasis. After a meal, when blood glucose levels rise, secretion of insulin lowers blood sugar by stimulating tissue glucose uptake (the primary tissue responsible being skeletal muscle). Conversely, when serum glucose levels fall secretion of glucagon stimulates the liver to release stored glucose into the blood stream.

Diabetes mellitus is an increasingly common disorder around the world, characterized by chronically elevated serum glucose levels. Classically, diabetes segregates into two distinct groups that require alternative therapeutic approaches. Type 1 diabetes, as known as insulin-dependent diabetes mellitus, is primarily caused by an inability of the subject to produce sufficient insulin to regulate blood sugar. On the other hand, type 2 diabetes, non-insulin-dependent diabetes, is characterized by an inability to respond to elevated serum insulin, a state know as insulin resistance. Both diabetic conditions are greatly exacerbated by clinical obesity, and likewise obesity is a risk factor to the development of type 2 diabetes.

Insulin resistance is a characteristic feature in the pathogenesis of diseases such as type 2 diabetes, metabolic syndrome, nonalcoholic fatty liver disease, polycystic ovarian syndrome and obesity though the molecular mechanisms causing these diseases are not fully understood (Spiegelman and Flier, 2001; Friedman, 2004; Bouche et al., 2004; Evans et al., 2004; Bhatia 2005; Bugianesi et al., 2005). However, impaired whole body glucose uptake plays a significant role in insulin resistance (Seely and Olefsky, 1993; Shulman, 2000; Virkamaki et al., 1999). Skeletal muscle constitutes the largest insulin-sensitive tissue mammals and thus insulin resistance in this organ has the largest impact on whole body glucose homeostasis (Shulman, 2004; Zierath et al., 2000). Although major advances have been made in the molecular mechanisms of insulin action in muscle, little is known of local muscle factors that can modulate glucose transport. Recently however, it was shown that mice lacking the protein corticotropin-releasing factor receptor 2 (CRFR2) displayed changes in insulin-sensitivity, suggesting a possible role for CRFR2 in blood sugar homeostasis (Bale et al., 2003). Additionally, CRFR2 is expressed as a variety of protein isoforms (CRFR2α, CRFR2β, CRFRγ), some of which are selectively expressed in certain tissues (Kostich et al., 1998). In general, it is known that CRFR2 is primarily expressed in heart and skeletal muscle. However, the role of CRFR2 signaling in regulation of serum glucose levels was still unclear (Perrin and Vale, 1999; Chen et al., 2005).

Corticotropin releasing factor receptors are the physiological receptors for the corticotropin-releasing factor (CRF) family peptides that have been suggested to play a role in modulating energy homeostasis (Brown et al., 1982; Dallman et al., 1995; Bale et al., 2003; De Kloet, 2004). Urocortin 2 (Ucn 2), a recently identified member of the CRF family (Reyes et al., 2001; Hsu and Hsueh, 2001), is highly expressed in skeletal muscle though the physiological functions of Ucn 2 in this tissue are not known (Chen et al., 2004). Interestingly, the effects of Ucn 2 are primarily mediated through activation of its high affinity, membrane receptor CRFR2 (Perrin et al., 1995; Kishimoto et al., 1995). A related CRF family member Urocortin 3 also acts as a CRFR2 agonist, and is expressed primarily in the pancreas. The invention described herein elucidate the role CRFR2 signaling in regulation of serum glucose homeostasis and insulin-sensitivity.

SUMMARY OF THE INVENTION

Reduced cellular insulin-sensitivity and increased serum insulin levels are the primary problem among individuals with type 2 diabetes, metabolic syndrome, nonalcoholic fatty liver disease, polycystic ovarian syndrome and obesity. The instant invention involves methods for enhancing the insulin-sensitivity of a cell and/or reducing serum insulin levels which are of use in the treatment of such individuals. It has been determined that CRFR2 activation plays a crucial role in decreasing insulin-sensitivity and stimulating insulin secretion in mammalian cells. In general, the invention provides methods for reducing or inhibiting CRFR2 signaling and thus increasing the amount of active insulin receptor substrate 1 (IRS-1) in a cell thereby increasing the insulin-sensitivity of the cell. Furthermore, the invention provides methods for reducing or inhibiting CRFR2 signaling thereby limiting or decreasing insulin secretion. Thue, a method for increasing insulin-sensitivity and/or decreasing insulin secretion in a subject in need of such therapy may comprise administering to the subject an amount of a composition comprising a corticotropin releasing factor receptor 2 (CRFR2) antagonist that is effective to reduce CRFR2 signaling. Methods of the invention involve both direct and indirect blockade of CRFR2 signaling. For example, CRFR2 signaling can be directly reduced by administering a CRFR2 antagonist that binds to CRFR2 or by reducing the expression of CRFR2 in the cell. Alternatively or in conjunction, CRFR2 signaling can be indirectly reduced by interfering with CRFR2 agonism. For example, a CRFR2 antagonist may be an antibody that binds to a CRFR2 agonist and can be used to block the CRFR2 agonist from binding to CRFR2. In other aspects, expression of CRFR2 agonists, such as Ucn 2 or Ucn 3 may be reduced in order to block CRFR2 agonism.

Thus, in certain embodiments, there is provided a method for regulating glucose homeostasis in a subject, for example by increasing insulin-sensitivity in the subject. Insulin-sensitivity may be increased by reducing or inhibiting CRFR2 signaling in the subject. As used herein the term "insulin-sensitivity" refers to ability of a subject to reduce serum glucose levels in response to increased levels of insulin. In certain cases, methods according to the invention will comprise reducing corticotropin releasing factor receptor 2 (CRFR2) signaling in skeletal muscle, the greatest mass of insulin sensitive tissue in mammalian subjects. In preferred embodiments, the subject may be a human. In some specific cases increasing insulin-sensitivity in the skeletal muscle is by blocking Ucn 2 agonism of CRFR2. Furthermore, since CRFR2 is also expressed in the CRFR2 antagonists may have additional neurological effects. Thus, in some embodiments, preferred CRFR2 antagonist for use according to the invention are antagonist that do not cross the blood-brain barrier and thus effect CRFR2 signaling only in peripheral tissues. Such antagonists may for example be polypeptides antagonists.

In some aspects, the invention provides a method for regulating glucose homeostasis in a subject by reducing or limiting insulin secretion in a subject. Reducing or limiting insulin secretion in a subject may be accomplished by reducing or inhibiting CRFR2 signaling in the subject. It will be understood "reducing insulin secretion in a subject" can mean reducing serum insulin levels or reducing insulin secretion in response to increased serum glucose levels (i.e., glucose dependent insulin secretion). In certain aspects of the invention there is provided a method for reducing or limiting insulin secretion in a subject by reducing or inhibiting CRFR2 signaling in the pancreas. Thus, in certain cases, insulin secretion can be reduced by blocking Ucn 3 agonism of CRFR2 in the pancreas.

It will also be understood that, in some embodiments, the invention provides a method for treating mammalian diseases that that involve insulin resistance and/or chronic elevation of serum insulin levels. Thus, the inventions provided methods to treat and/or prevent the pathologic onset of type 2 diabetes, metabolic syndrome, nonalcoholic fatty liver disease and/or polycystic ovarian syndrome in a subject. These methods may involve increasing insulin-sensitivity in the subject and/or reducing insulin secretion in the subject (or total serum insulin level). As described above methods of the invention involve reducing or inhibiting CRFR2 signaling in the subject. In certain embodiments, methods according the invention can be used to delaying the onset of a disease, such as type 2 diabetes, in a subject at risk for developing the disease or with a genetic predisposition for such a disease. As used here "at risk" subjects can include but is not limited to obese subjects or aged individuals. Furthermore, at risk subjects may have chronic elevated blood insulin, triglycerides or glucose levels and/or have high blood pressure.

In yet further aspects of the instant invention, there is provided a method of reducing the mass of adipose tissue in an individual by reducing CRFR2 signaling. Similarly, there is provided a method for increasing the mass of lean tissue in an individual by reducing CRFR2 signaling. Thus, it will be understood that in certain aspects of the invention "reducing the mass of adipose tissue" or "increasing the mass of lean tissue" in an subject may comprise increasing the ratio of lean tissue to fatty tissue in the subject. Methods according to this aspect of the invention may be of particular use in individuals with clinical obesity, those on a high fat diet or individuals that maintain high serum HDL or triglyceride levels.

In certain aspects of the invention, reducing CRFR2 signaling in a subject is by administering a CRFR2 antagonist to the subject. As used herein the term "CRFR2 antagonist" means a molecule that inhibits or reduces its signaling in response to CRFR2 agonists. In some instances, an antagonist molecule binds to CRFR2 and inhibits or reduces its intrinsic signaling ability. Thus, CRFR2 antagonist can be polypeptides, nucleic acids, such as aptamers or small molecules. In certain other cases, CRFR2 antagonists may not bind directly to CRFR2, for example a CRFR2 antagonist may bind to and inhibit a CRFR2 agonist or reduce the expression of CRFR2 or a CRFR2 agonist.

In some very specific cases, a CRFR2 antagonist is a modified CRF family member that can bind to CRFR2 but is unable to activate (or has reduced ability to activate) CRFR2 signaling. Is has been shown that modified versions of CRF family members with N-terminal amino acid deletions can act as CRFR antagonists (Rivier et al., 2002; Rijkers et al., 2004). Thus in some embodiments, a CRFR2 antagonist may be highly homologous to a CRF family member but have a N-terminal deletion. For example, N-terminal deletions can be made in human CRF (SEQ ID NO:12), frog sauvagine (SEQ ID NO:9), human Ucn 2 (SEQ ID NO:1), mouse Ucn 2 (SEQ ID NO:4), human Ucn 3 (SEQ ID NO:2), mouse Ucn 3 (SEQ ID NO:3) human Ucn 1 (SEQ ID NO:20) or mouse Ucn 1 (SEQ ID NO:21) in order to generate a CRFR2 antagonist. In some cases, these antagonists may additionally comprise one or more conservative amino acid substitutions and/or an amino acid may be substituted for an amino acid at the same position in one of the other CRF family members (Rivier et al., 2002; U.S. Pat. No. 6,953,838). For example, such amino acid substitutions can be made to confer acid stability to the polypeptide, this is particularly preferred when polypeptides are administered orally. Additionally, in preferred embodiments, modified CRF family members are aminated on at the carboxyl-terminus.

It is contemplated that in some cases, a CRFR2 antagonist may also act as a CRFR1 antagonist. For example, modified CRF family members that act as CRFR1 and CRFR2 antagonist have been previously described in by Rivier et al., 2002 and U.S. Pat. Nos. 6,323,312, 5,874,227, 5,777,073, 5,510,458, 5,245,009 and 5,109,111. Additionally, certain antibody CRFR2 antagonists may additionally act a CRFR1 antagonists. Such antibodies may recognize an epitope shared between the two proteins, or it may a bispecific antibody that comprises binding domains specific for both CRFR1 and CRFR2.

In certain preferred embodiments, a CRFR2 antagonist according to the current invention is a specific antagonist that has greater antagonist activity on CRFR2 relative to CRFR1. For example, in some cases, preferred CRFR2 antagonists exhibit at least about two, three, four, five, ten or greater fold selectivity for CRFR2 (e.g., such molecules inhibit CRFR2 signaling at least about two, three, four, five or ten fold lower concentrations than the concentration required for similar inhibition of CRFR1 signaling). Thus, in certain embodiments, a CRFR2 selective antagonist has no significant antagonist activity on CRFR1. For instance, CRFR2 antagonists that do not have significant binding affinity for CRFR1 have been described by Rivier et al. (2002). In some very specific cases these antagonists may be modified frog sauvagine polypeptides according the general sequence:

```
                                              (SEQ ID NO:13)
[DPhe-His-(Leu or CαMeLeu)-Leu-Arg-(Lys or Glu)-

(Met, Nle or Val)-(Ile Leu)-Glu-(Ile or Nle)-(Ala or Glu)-(Lys or Arg)-(Gln or Ala)-Glu-(Gln or
```

-continued

Lys)-(Glu or Leu)-(Lys or Ala)-Gln-Gln-Ala-(Ala, Gln, Glu or Glu linked to Lys$^{24}$ via a lactam bridge)-(Asn or Ser)-Asn-(Arg, Lys(Ac), Lys, Lys linked to Glu$^{21}$ via a lactam bridge or Glu linked to Lys$^{27}$ via a lactam bridge)-(Leu or Lys)-Leu-(Leu, Nle or Lys linked to Glu$^{24}$ via a lactam bridge)-(Asp or Glu)-(Ile or CαMeLeu)-Ile-NH$_2$]

Thus in very specific cases, a modified sauvagine polypeptide may be Antisauvagine-30 (SEQ ID NO:11), astressin$_2$B (SEQ ID NO:10), Cyclo(32-35)[DPhe$^{12}$,Nle$^{21,38}$,Glu$^{32}$, Lys$^{35}$]-hCRF$_{(12-41)}$ (SEQ ID NO:14), Cyclo(31-34)[DPhe$^{11}$, His$^{12}$,C(α)MeLeu$^{13,39}$,Nle$^{17}$,Glu$^{31}$,Lys$^{34}$]Ac-Sauvagine$_{(8-40)}$ (SEQ ID NO:15), Linear [DPhe$^{11}$,His$^{12}$,C(α)MeLeu$^{13,39}$,Nle$^{17}$,Glu$^{31}$,Lys$^{34}$]Ac-Sauvagine$_{(8-40)}$ (SEQ ID NO:16), Linear [DPhe$^{11}$,His$^{12}$,C(α)MeLeu$^{13,39}$,Nle$^{17}$, Gln$^{31}$,Lys(Ac)$^{34}$]Ac-Sauvagine$_{(8-40)}$ (SEQ ID NO:17), Cyclo(34-37)[DPhe$^{11}$,His$^{12}$,C(α)MeLeu$^{13,39}$,Nle$^{17}$,Glu$^{34}$, Lys$^{37}$]Ac-Sauvagine$_{(8-40)}$ (SEQ ID NO:18) or Linear [DPhe$^{11}$,His$^{12}$,C(α)MeLeu$^{13,39}$,Nle$^{17}$,Gln$^{31}$,Lys(Ac)$^{34}$]Ac-Sauvagine$_{(11-40)}$ (SEQ ID NO:19) (see Rivier et al., 2002).

In some further embodiments CRFR2 antagonists may be modified Ucn 3 polypeptides. For example, a Ucn 3 polypeptides comprising a five to eight amino acids deletion in the amino terminus. Such polypeptides may comprises sequences from human Ucn 3 (SEQ ID NO:2), mouse Ucn 3 (SEQ ID NO:3) or may be a human or mouse Ucn 3 wherein one or more amino acids have been substituted for amino acids with a similar hydrophilicity. In certain cases, a modified Ucn 3 polypeptide may be a human Ucn 3 polypeptide wherein one or more amino acids has been substituted for an amino acid in the same position of mouse Ucn 3. In certain very specific cases, a modified Ucn 3 polypeptide may comprise one or more amino acid substitutions selected from Leu7, Nle7, Thr8, Ile9, DPhe9, Phe9, Gly10, His10, Leu11, Nle1, CαMeLeu11, Leu12, Nle12, Arg13, Gln13, Nle14, CαMeLeu14, Nle15, CαMeLeu15, CαMeLeu16, Leu16, Nle16, Glu17, Asp17, Nle18, Leu18, Arg20, Nle24, CαMeLeu24, Glu29, Gln29, Arg32, Lys32, Lys(Ac)32, Ile34, Nle34, CαMeLeu34, Leu35, Nle35, Asp36, Glu36, CαMeLeu37 or Val38. Such an analog can be derived by comparison of the Ucn 3 sequence with other corticotropin releasing factor homologs, and astressin2B. Additionally, a Ucn 3 polypeptide antagonist may be structurally constrained by the formation of a lactam ring, for example between Glu29 and Lys32 in a Ucn 3 analog (Rivier et al., 2002). Thus, it will be understood by on of skill in the art that any of the Ucn 3 CRFR2 antagonists described in U.S. Pat. No. 6,953,838 may be used in methods according to the current invention.

In further cases, some preferred CRFR antagonists are modified Ucn 2 polypeptides. For example, Ucn 2 polypeptides comprising a five to eight amino acids deletion in the amino terminus. Such polypeptides may comprise sequences from human Ucn 2 (SEQ ID NO:1), mouse Ucn 2 (SEQ ID NO:4) or may be a human or mouse Ucn 2 wherein one or more amino acids have been substituted for amino acids with a similar hydrophilicity. In certain cases, a modified Ucn 2 polypeptide may be a human Ucn 2 polypeptide wherein one or more amino acids has been substituted for an amino acid in the same position of mouse Ucn 2. In certain very specific cases, a modified Ucn 2 polypeptide may comprise one or more amino acid substitutions selected from Leu7, Nle7, Thr8, Ile9, DPhe9, Phe9, Asn10, His10, Ile11, Nle11, CαMeLeu11, Nle12, Asn13, Gln13, Nle14, CαMeLeu14, Nle15, CαMeLeu15, CαMeLeu16, Phe16, Nle16, Asn17, Asp17, Nle18, Leu18, Lys20, Nle24, CαMeLeu24, Glu29, Gln29, Arg32, Lys32, Lys(Ac)32, Ile34, Nle34, CαMeLeu34, Leu35, Nle35, Asp36, Glu36, CαMeLeu37 and Val38. Such analogs can be derived by comparison of the Ucn 2 sequence with other corticotropin releasing factor homologs, and Asstressin2B. Additionally, a Ucn 2 polypeptide antagonist may be structurally constrained by the formation of a lactam ring, for example between Glu29 and Lys32 in a Ucn 2 analog (Rivier et al., 2002).

CRFR2 antagonists may also comprise antibodies or aptamers that bind to CRFR2 and inhibit or decrease its activity. For example, an antibody or apatamer CRFR2 antagonist may bind to CRFR2 and inhibit the binding or agonism mediated by Ucn 2 or Ucn 3. The term antibodies includes, but is not limited to, polyclonal antibodies, monoclonal antibodies, antibody fragments, such as Fab fragments, single chain antibodies and humanized antibodies. Antibodies can be made by any of the methods well known to those of skill in the art and as further described in the detailed description of the embodiments. As used herein the term "aptamer" mean a nucleic acid molecule that is capable of binding to a specific ligand (i.e., CRFR2). Thus, it will be understood that in certain circumstances a CRFR2 antagonist may be an antibody or an aptamer that binds to one or more of the CRFR2 protein isoforms. However, in certain preferred embodiments antibodies and aptamers according to the invention may be specific for one or more of the CRFR2 protein isoforms. Thus, in certain cases, antibodies and/or aptamers may bind to a portion of CRFR2 that comprises amino acid sequence that is unique to a given CRFR2 isoform. For example, the antibody or amptamer may bind to unique amino acids of CRFR2α (i.e. SEQ ID NO:26), CRFR2β (i.e. SEQ ID NO:27), or CRFR2γ (i.e. SEQ ID NO:28). Thus, in preferred embodiments of the invention, a CRFR2 antagonist will be an aptamer or antibody that selectively binds to a particular CRFR2 protein isoform thereby reducing or inhibiting CRFR2 signaling.

Another method for reducing CRFR2 signaling in the subject is by reducing CRFR2 expression. For example, in some cases CRFR2 expression may be reduced by administering a CRFR2 specific small interfering nucleic acid (siNA). For instance, an siNA molecule may comprise 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more nucleotides that are complementary to the sequence of human CRFR2α (SEQ ID NO:7), CRFR2β (SEQ ID NO:24) and/or CRFR2γ (SEQ ID NO:22) (corresponding to NCBI accession nos. AY449734, AF011406 and AF019381 respectively). In certain very specific embodiments, siNAs according to the invention may be complementary to CRFR2 nucleic acid sequences that are unique to a specific CRFR2 isoform. Thus, in a preferred embodiment, siNAs according to the invention may comprise sequences that are complementary to unique portions of CRFR2α mRNA (i.e. SEQ ID NO:29), CRFR2β mRNA (i.e. SEQ ID NO:30), and/or CRFR2γ mRNA (i.e. SEQ ID NO:31). In some embodiments of the invention, methods for reducing CRFR2 signaling are specific for one or more of the CRFR2 isoforms.

In still further aspects of the invention, CRFR2 signaling may be reduced or inhibited indirectly. For example, indirect reduction of CRFR2 signaling may be by blockade of CRFR2 agonists. In some cases, polypeptides that bind to Ucn 2 or Ucn 3 can be used to block Ucn 2 or Ucn 3 receptor agonism. Thus, in certain embodiments, it is contemplated that antibodies that bind to both Ucn 2 and Ucn 3 via a common epitope may be used. However, in some preferred cases, antibodies that selectively bind to Ucn 2 or Ucn 3 can be used according to the method of the invention. As indicated above the term "antibody" as used here includes but is not limited to polyclonal antibodies, monoclonal antibodies, antibody fragments, such as Fab fragments, single chain antibodies, and humanized antibodies. Thus, in some cases, antibodies that reduce CRFR2 signaling are antibodies that are generated by immunizing an animal with a Ucn 2 or Ucn 3 polypeptide. In a very specific example, the antibody may be a Ucn 3 binding antibody, such as the PBL #6570 antibody described herein. Other polypeptides for use in methods of to the invention include but are not limited to soluble CRF receptors. For example, the extra cellular portions of the CRFR2 may be used to inhibit CRFR2 signaling. Polypeptides for use in such methods are described in U.S. provisional patent application No. 60/650,866 (now U.S. application Ser. No. 11/350,411, now U.S. Pat. No. 7,507,794), incorporated herein by reference. Furthermore, the extracellular domains of any of the CRFR2 protein isoforms according to SEQ ID NO:7, SEQ ID NO:24 and/or SEQ ID NO:22 may be used to inhibit CRFR2 signaling. Thus, methods according to the invention may comprise indirectly reducing CRFR2 signaling by administering polypeptides that bind to Ucn 2 and/or Ucn 3 and in certain case may involve polypeptides that bind selectively to Ucn 2 or Ucn 3.

Further methods for indirectly reducing CRFR2 signaling in a subject may include, but are not limited to, reducing the expression of a CRFR2 agonist. For example, CRFR2 signaling may be reduced by reducing the expression of urocortin 2. In some case urocortin 2 expression may be reduced by administering a composition comprising urocortin 2 specific siNA. In certain cases, an siNA molecule may comprise 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more nucleotides that are complementary to the sequence of human Ucn 2 (SEQ ID NO:5). In still other examples, CRFR2 signaling may be reduced by reducing the expression of Ucn 3. Ucn 3 expression can be reduced by administering a composition comprising Ucn 3 specific siNA. For example, an siNA molecule may comprise 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more nucleotides that are complementary to the sequence of human Ucn 3 (SEQ ID NO:6).

Methods according to the instant invention may also be used in combination with other therapeutic strategies that are known to those of skill in the art. For example, in certain embodiments methods according the instant invention may be used in combination with insulin administration. In this case, such methods may reduce the amount of insulin that must administered and/or the frequency at which the insulin is administered. Other compounds that are known in the art to be effective for regulating glucose homeostasis include sulfonylureas, alpha-glucosidase inhibitors, thiazolidinediones, motformin and repaglinide. Thus, methods of the invention may additionally comprise, administering a sulfonylurea, an alpha-glucosidase inhibitor, a thiazolidinedione, motformin, or repaglinide to a the subject. Combination treatment may be particularly preferred as they can reduce the effective concentrations of each therapeutic compound used and thus limit undesirable side effects of the compounds.

Embodiments discussed in the context of a methods and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

DETAILED DESCRIPTION OF THE INVENTION

Figure 1:
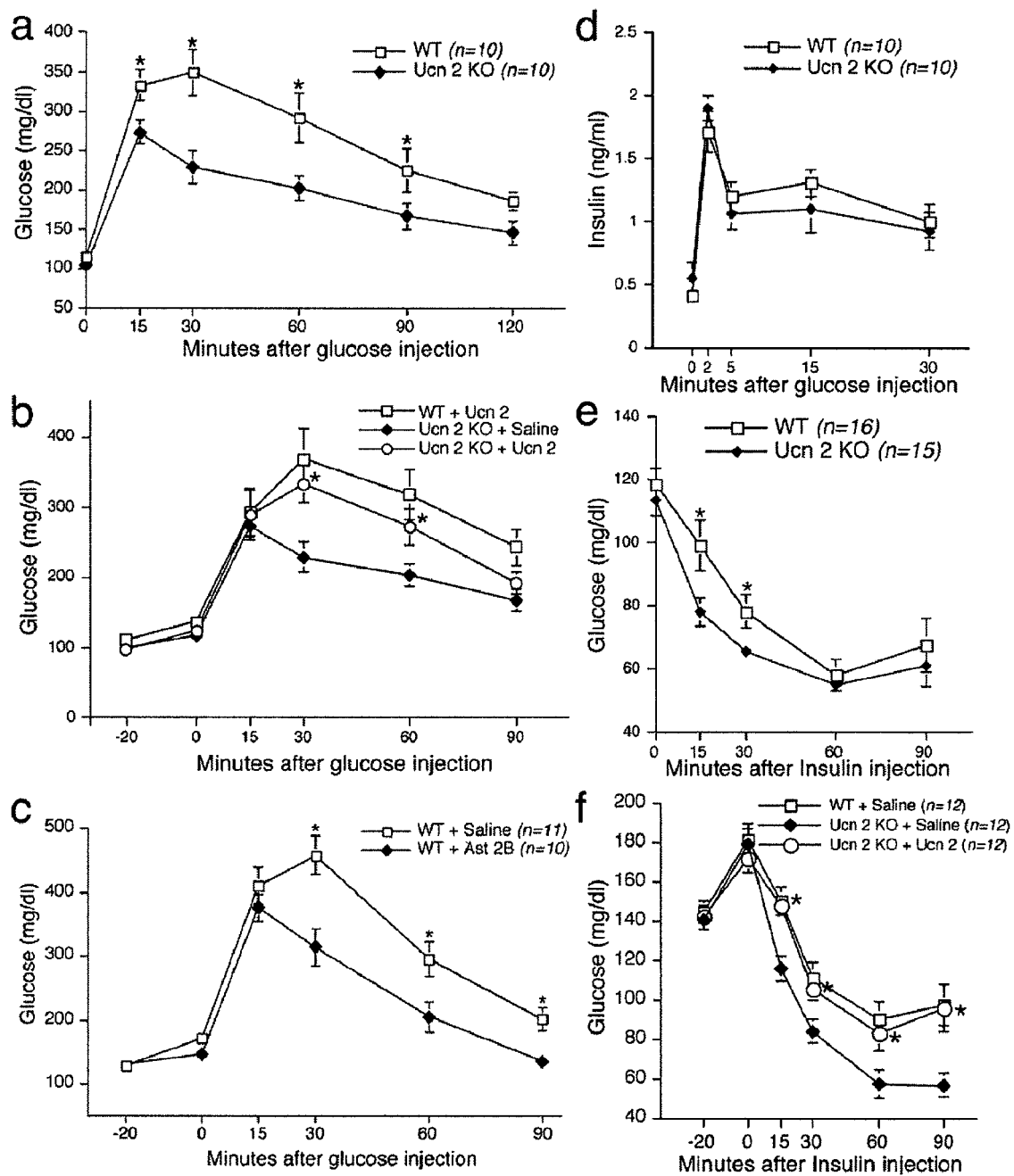
FIG. 1a-f: Metabolic phenotype of Ucn 2 null mice. (a) Ucn 2-null mice demonstrate enhanced glucose tolerance. The ability of the Ucn 2 null mice and wild type littermates to handle a glucose load was assessed using a standard glucose tolerance test (see example 1). Fasted male mice were injected intraperitoneally (IP) with glucose (2 g/kg body weight) and blood glucose levels were measured before and at 15, 30, 60, 90 and 120 min following glucose injection. (b) Administration of synthetic Ucn 2 peptide to mutant mice prior to the glucose tolerance test restores blood glucose to wild type levels. Fasted male Ucn 2 null mice were injected IP with saline or with 0.1 μg/kg body weight Ucn 2, 20 min prior to glucose injection (2 g/kg body weight) and blood glucose levels were measured before and at 15, 30, 60 and 90 min following glucose injection. (c) Administration of the CRFR2 specific antagonist astressin$_2$B into wild type mice mimics the Ucn 2 mutant mice glucose tolerance test profile. Fasted male wild type mice were injected IP with saline or with astressin$_2$B (30 μg/kg body weight), 20 min prior to glucose injection (2 g/kg body weight), and blood glucose levels were measured before and at 15, 30, 60 and 90 min following glucose injection. (d) The enhanced glucose tolerance in the Ucn 2 null mice is not due to increased insulin secretion. Fasted male mice were injected with glucose (3 g/kg body weight, IP) and blood samples were collected at 2, 5, 15 and 30 min following glucose injection and insulin was measured by radioimmunoassay. (e) Ucn 2-null mice demonstrate increased insulin-sensitivity using the insulin tolerance test. Fasted male mice were injected with insulin (0.75 U/kg body weight, IP) and blood glucose levels were measured before and at 15, 30, 60 and 90 min following insulin injection. (f) Administration of synthetic Ucn 2 peptide to mutant mice, prior to the insulin tolerance test, restores blood glucose to wild type levels. Fasted male Ucn 2 null mice were injected with saline or Ucn 2 peptide (0.1 μg/kg body weight, IP), 20 min prior to insulin injection (0.75 U/kg body weight), and blood glucose levels were measured before and at 15, 30, 60 and 90 min following insulin injection. In each case "KO" indicates Ucn 2 null mice.

The instant invention involves methods for regulating metabolic homeostasis in a subject. These methods are particularly applicable to subjects insulin resistance and/or chronically elevated serum insulin levels, such as subjects with type 2 diabetes, metabolic syndrome, nonalcoholic fatty liver disease, polycystic ovarian syndrome and obesity. For example methods are provided for lower serum insulin levels and increasing insulin-sensitivity in a subject. Specifically, methods according to the current invention involve reducing or inhibiting CRFR2 signaling, for example by the administration of a CRFR2 antagonist.

I. CRFR2 Antagonists

It is contemplated that in some cases a CRFR2 antagonist may be administered to reduce or inhibit CRFR2 signaling in a subject. In general the term "antagonist" as used here refers to a molecule that inhibits or reduces the activity of CRFR2. In this case CRFR2 activity is the intra cellular signaling cascade that is activated by binding of the CRFR2 agonist such as Ucn 2 or Ucn 3. Thus, in some respects a CRFR2 antagonist may be a molecule that binds to CRFR2 and blocks or reduces the signaling of CRFR2 in response to Ucn 2 or Ucn 3. Such CRFR2 binding molecules may be antibodies or aptamers to CRFR2, modified CRF family member polypeptides or small molecules. In certain other respects, CRFR2 antagonists may be molecules that do not bind to CRFR2 however are able to reduce or inhibit signaling of CRFR2. For example, molecules that bind to Ucn 2 or Ucn 3 and inhibit the ability of one or both molecules to activate CRFR2 signaling. Alternatively, CRFR2 antagonist molecules may reduce the expression of Ucn 2, Ucn 3, and/or CRFR2 thereby reducing CRFR2 signaling. An example of such a molecule being an siNA molecule directed to Ucn 2, Ucn 3, and/or CRFR2 nucleotide sequences. Thus, the instant invention provides a variety of methods for use in reducing CRFR2 signaling in cells and thereby modulating metabolic homeostasis in a subject.

1. Modified CRF Family Members

As discussed above, in some respects CRFR2 antagonist comprise modified CRF family members that bind to CRFR2 but reduce or inhibit signaling in response to a CRFR2 agonist. For instance, a modified CRF family member may bind to CRFR2, however not activate or minimally activate CRFR2 signaling. These antagonists may either disrupt CRFR2-agonist interaction or allow the CRFR2 agonist to bind, but inhibit the ability of the agonist to activate CRFR2 signaling. Thus, it will be understood that in certain embodiments the CRFR2 antagonist may be a CRF family member with one or more modification that allows it bind to CRFR2 and inhibit CRFR2 activation by agonist molecules.

A variety of CRF family members are known that can be modified in order to act as CRFR2 antagonists. These molecules can be derived from the CRF family member of variety of organisms such as mice, rats, humans and frogs. Some non limiting examples of CRF family members include human and mouse Ucn 3 (SEQ ID NO:2 and SEQ ID NO:3), human and mouse Ucn 2 (SEQ ID NO:1 and SEQ ID NO:4), human and mouse Ucn 1 (SEQ ID NO:20 and SEQ ID NO:21), frog sauvagine (SEQ ID NO:9) and human CRF (SEQ ID NO:12). Modifications of these polypeptides may comprise amino acid deletions, amino acid insertions, amino acid substitutions and/or chemical changes, such as the insertion of lactam bridges, acetylation of amino acid side chains or addition of PEG to the polypeptide. In general, modification are made to accomplish one or more of the following; to reduce CRFR2 activation by the molecule, to enhance the molecules ability to block CRFR2 antagonism, to enhance CRFR2 binging of the molecule or to modify the pharmacokinetics of the molecule. Thus, it will be understood that while any CRF family member can be modified in order to generate a CRFR2 antagonist, CRF family members with high affinity for CRFR2 are preferred as CRFR2 antagonists.

In certain embodiments, preferred CRFR2 antagonists are modified CRF family members that bind to CRFR2 but have a lower binding affinity for CRFR1. In particular CRFR2 specific antagonist may be effective at lower concentrations and have fewer side effects that antagonists that bind at high affinity to both CRFR1 and CRFR2. In this respect, it may also be preferable that CRF family members be modified so as to reduce their affinity for CRFR1. Methods for testing the affinity of such modified CRF family members are described in detail in Rivier et al., 2002. However, one approach is to modify CRF family members that already have higher affinity for CRFR2 than CRFR1, thus in certain aspects CRFR2 antagonists are modified Ucn 1, Ucn 2, or Ucn 3 polypeptides.

It is also contemplated that in certain embodiments modified CRF family member will preferentially antagonize specific CRFR2 protein isoforms. For example, the affinity of modified CRF family members for the alpha, beta and/or gamma protein isoforms for CRFR2 can assessed and CRFR2 antagonists that are specific for one or more of the isoforms can be selected. This may be of particular advantage since it is known that the expression of the various CRFR2 isoforms varies and thus by targeting specific CRFR2 isoforms organs or tissues expressing that isoform may be more specifically targeted. Again, this kind of specific CRFR2 isoform targeting can both increase the efficacy and decrease potential side effects of CRFR2 antagonists.

As discussed above modified CRF family members may be used according to the invention as CRFR2 antagonists. The goal of making such modifications are may fold, and comprise increasing CRFR2 affinity, decreasing activation of CRFR2, modifying the affinity of the polypeptide for specific CRFR2 isoforms, enhancing the ability of the polypeptide to block CRFR2 agonism and enhancing the pharmacokinetics of the CRFR2 antagonist. A variety of modifications can be employed to accomplish these goals and in each case the effect of the modification on various aspects of CRFR2 agonist activity can be assessed.

It is well known in the art that amino terminal deletions of CRF family member can result in polypeptides that have antagonist activity, for example see River et al. 2002, Rijker et al., 2004 and U.S. Pat. Nos. 6,323,312, 5,874,227, 5,777,073, 5,510,458, 5,245,009 and 5,109,111. Thus in certain embodiments, modified CRF polypeptides will comprise a deletion of amino terminal amino acid sequence. Preferred CRF polypeptides comprise deletions of the first five, six, seven or eight amino acids of mature CRF polypeptide sequence. Thus it will be understood, that in some embodiments a CRFR2 antagonist will be a CRF polypeptide, such as human and mouse Ucn 3 (SEQ ID NO:2 and SEQ ID NO:3), human and mouse Ucn 2 (SEQ ID NO:1 and SEQ ID NO:4), human and mouse Ucn 1 (SEQ ID NO:20 and SEQ ID NO:21), frog sauvagine (SEQ ID NO:9) and human CRF (SEQ ID NO:12) wherein the polypeptide comprises a deletion of the first five to eight amino acids.

In additional aspects of the invention CRF polypeptides may be further modified by amino substitutions, for example by substituting an amino acid at one or more positions with an amino acid having a similar hydrophilicity. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in CRFR2 antagonists and will likely only have minor effects on their activity and ability to bind CRFR2. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the polypeptide CRFR2 antagonist described herein may be modified by the substitution of an amino acid, for different, but homologous amino acid with a similar hydrophilicity value. Amino acids with hydrophilicities within +/−1.0, or +/−0.5 points are considered homologous.

It will also be understood that certain amino acids have specific properties, and thus any amino acid substitution will abolish said property. For example cysteine residues have the unique ability to form di-sulfide bonds, that can be crucial for protein structure and activity. Thus, a substitution of cysteine residue for any other amino acid may be expected, by one of skill in the art, to alter the activity of a protein. Additionally, certain CRFR2 antagonists are may also comprise a lactam bridge that structurally constrain the polypeptide. Such lactam bridges can be formed between Glu and Lys residues in a protein, and thus in certain cases amino acids may be substituted for a Glu or a Lys in order to facilitated the insertion of a lactam bridge. Such lactam bridges have been shown to be very effective in the generation of CRFR2 antagonist as described in Rivier et al., 2002. Therefore in certain embodiments specific amino acids may be substituted for unlike amino acids in order to facilitate the insertion of an amino acid with a desired chemical or structural property, such as a lactam bridge.

Thus, further aspects of the invention modified CRF polypeptides may or more modified or unusual amino acids such as those listed in Table 1. For example norleucine, a non-templated amino acid that is formed by deamination of lysine, may be substituted at one or more positions. In certain cases CRF polypeptides of the invention may incorporate amino acids of the "D" chirality that do not naturally occur in proteins, and are thereby resistance to degradation. In each case such an amino acid is indicated by the letter "D" proceeding the three letter abbreviation of the amino acid. For D-Phenylalanine is indicated by DPhe. As discussed above polypeptides according to the invention may also be cyclic, for example Glu and Lys residues may be linked by a lactam bridge (see Rijker et al., 2004; Rivier et al., 2002).

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | Lys(Ac) | Acetylated-lysine |
| Baib | 3-Aminoisobutyric acid | MeGly | N-Methylglycine, sarcosine |
| Apm | 2-Aminopimelic acid | MeIle | N-Methylisoleucine |
| CαMeLeu | alpha-methyl leucine | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In still further embodiments, CRFR2 antagonists may be CRF polypeptides further modified by amino acid substitutions wherein an amino acid a given position is substituted for an amino acid at the same position in a different CRF family member. These types of substitutions have been previously described in Rivier et al., 2002 and U.S. Pat. No. 6,953,838. Previous studies have defined certain substitutions and chemical modifications that enhance binding of CRF family members to CRFR2.

Thus, it will be understood that some particularly preferred modified CRF polypeptides are specific CRFR2 antagonist that do not bind to CRFR1. Some exemplary sequences comprise modified frog sauvagine polypeptides according the general sequence (in each case amino acid numbering is bases on the wild type sequence for the indicated mature CRF family member polypeptide):

```
                                            (SEQ ID NO:13)
[DPhe-His-(Leu or CαMeLeu)-Leu-Arg-(Lys or Glu)-

(Met, Nle or Val)-(Ile Leu)-Glu-(Ala or Glu)-(Lys or Arg)-(Gln or Ala)-Glu-(Gln or Lys)-(Glu or

Leu)-(Lys or Ala)-Gln-Gln-Ala-(Ala, Gln, Glu or

Glu linked to Lys24 via a lactam bridge)-(Asn or

Ser)-Asn-(Arg, Lys(Ac), Lys, Lys linked to Glu21 via a lactam bridge or Glu linked to Lys27 via a lactam bridge)-(Leu or Lys)-Leu-(Leu, Nle or Lys linked to Glu24 via a lactam bridge)-(Asp or Glu)-

(Ile or CαMeLeu)-Ile-NH2]
```

Thus in very specific cases, a modified sauvagine polypeptide may be Antisauvagine-30 (SEQ ID NO:11), astressin$_2$B (SEQ ID NO:10), Cyclo(32-35)[DPhe$^{12}$,Nle$^{21,38}$,Glu$^{32}$, Lys$^{35}$]-hCRF$_{(12-41)}$ (SEQ ID NO:14), Cyclo(31-34)[DPhe$^{11}$, His$^{12}$,C(α)MeLeu$^{13,39}$,Nle$^{17}$,Glu$^{31}$,Lys$^{34}$]Ac-Sauvagine$_{(8-40)}$ (SEQ ID NO:15), Linear [DPhe$^{11}$,His$^{12}$,C(α) MeLeu$^{13,39}$,Nle$^{17}$,Glu$^{31}$,Lys$^{34}$]Ac-Sauvagine$_{(8-40)}$ (SEQ ID NO:16), Linear [DPhe$^{11}$,His$^{12}$,C(α)MeLeu$^{13,39}$,Nle$^{17}$, Gln$^{31}$,Lys(Ac)$^{34}$]Ac-Sauvagine$_{(8-40)}$ (SEQ ID NO:17), Cyclo(34-37)[DPhe$^{11}$,His$^{12}$,C(α)MeLeu$^{13,39}$,Nle$^{17}$,Glu$^{34}$, Lys$^{37}$]Ac-Sauvagine$_{(8-40)}$ (SEQ ID NO:18) or Linear [DPhe$^{11}$,His$^{12}$,C(α)MeLeu$^{13,39}$,Nle$^{17}$,Gln$^{31}$,Lys(Ac)$^{34}$]Ac-Sauvagine$_{(11-40)}$ (SEQ ID NO:19) (see Rivier et al., 2002).

In some further embodiments CRFR2 antagonists may be modified Ucn 3 polypeptides. For example, Ucn polypeptides comprising a five to eight amino acids deletion in the amino terminus. The sequence of such polypeptides may comprises human Ucn 3 (SEQ ID NO:2), mouse Ucn 3 (SEQ ID NO:3) or may be a human or mouse Ucn 3 wherein one or more amino acids have been substituted for amino acids with a similar hydrophilicity. In certain cases, a modified Ucn 3 polypeptide may be a human Ucn 3 polypeptide wherein one or more amino acids has been substituted for an amino acid in the same position of mouse Ucn 3. In certain very specific cases a modified Ucn 3 polypeptide may comprise one or more amino acid substitutions selected from Leu$^7$, Nle$^7$, Thr$^8$, Ile$^9$, DPhe$^9$, Phe$^9$, Gly$^{10}$, His$^{10}$, Leu$^{11}$, Nle$^{11}$, CαMeLeu$^{11}$, Leu$^{12}$, Nle$^{12}$, Arg$^{13}$, Gln$^{13}$, Nle$^{14}$, CαMeLeu$^{14}$, Nle$^{15}$, CαMeLeu$^{15}$, CαMeLeu$^{16}$, Leu$^{16}$, Nle$^{16}$, Glu$^{17}$, Asp$^{17}$, Nle$^{18}$, Leu$^{18}$, Arg$^{20}$, Nle$^{24}$, CαMeLeu$^{24}$, Glu$^{29}$, Gln$^{29}$, Arg12, Lys32, Lys(Ac)$^{32}$, Ile$^{34}$, Nle$^{34}$, CαMeLeu$^{34}$, Leu$^{35}$, Nle$^{35}$, Asp$^{36}$, Glu$^{36}$, CαMeLeu$^{37}$ or Val38. Such analog can be derived by comparison of the Ucn 3 sequence with other corticotropin releasing factor homologs, and astressin$_2$B. Additionally, Ucn 3 polypeptide antagonist may be structurally constrained by the formation of a lactam ring, for example between Glu$^{29}$ and Lys$^{32}$ in a Ucn 3 analog (Rivier et al., 2002). Thus, it will be understood by on of skill in the art that any of the Ucn 3 CRFR2 antagonists described in U.S. Pat. No. 6,953,838 may be used in methods according to the current invention.

Some preferred further antagonists are modified Ucn 2 polypeptides. For example, Ucn polypeptides comprising a five to eight amino acids deletion in the amino terminus. The sequence of such polypeptides may comprises human Ucn 2 (SEQ ID NO:1), mouse Ucn 2 (SEQ ID NO:4) or may be a human or mouse Ucn 2 wherein one or more amino acids have been substituted for amino acids with a similar hydrophilicity. In certain cases a modified Ucn 2 polypeptide may be a human Ucn 2 polypeptide wherein one or more amino acids has been substituted for an amino acid in the same position of mouse Ucn 2. In certain very specific cases a modified Ucn 2 polypeptide may comprise one or more amino acid substitutions selected from Leu7, Nle7, Thr8, Ile9, DPhe9, Phe9, Asn10, His10, Ile11, Nle11, CαMeLeu11, Nle12, Asn13, Gln13, Nle14, CαMeLeu14, Nle15, CαMeLeu15, CαMeLeu16, Phe16, Nle16, Asn17, Asp17, Nle18, Leu18, Lys20, Nle24, CαMeLeu24, Glu29, Gln29, Arg32, Lys32, Lys(Ac)32, Ile34, Nle34, CαMeLeu34, Leu35, Nle35, Asp36, Glu36, CαMeLeu37 and Val38. Such analogs may be derived by comparison of the Ucn 2 sequence with other corticotropin releasing factor homologs, and astressin2B. Additionally, Ucn 2 polypeptide antagonist may be structurally constrained by the formation of a lactam ring, for example between Glu29 and Lys32 in a Ucn 2 analog (Rivier et al., 2002).

It will also be understood that modified CRF polypeptides may include additional residues, such as additional N- and/or C-terminal amino acids and yet still be essentially as set forth in one of the sequences disclosed herein. In certain cases, for example modified CRF polypeptide may comprise additional N- and/or C-terminal amino acids that can be chemically or proteolytically cleaved from the polypeptide. It will be understood that a peptides or polypeptides will typically comprise a free amino group at the amino terminus and a free carboxy group at the carboxy terminus. However, since these groups remain reactive in a variety of chemistries it is often preferred that the amino terminus, the carboxy terminus, or both termini of a peptide or polypeptide be blocked or protected by addition of a less reactive group. For example, the amino terminus of a modified CRF polypeptide may be blocked by an acyl group. In preferred embodiments, a peptide and/or polypeptide of the invention may comprises a dibenzyl oxy carboxyl group or an acetylated residue at the amino terminus. Thus, in some cases the —NH$_2$ terminus is replaced with —NH—CO—CH$_2$. In certain cases, a modified peptide or polypeptide may additionally or independently comprise an amidated (e.g., the —COOH group is replaced by —CO—NH$_2$) or esterified carboxy terminal residue. Thus, in some highly preferred aspects, a peptide or polypeptide will comprise both an amino terminal acetylated residue and a carboxy terminal amidated residue. For instance, modified CRF family members may preferably be aminated at the carboxyl terminus, as is the case in naturally occurring, mature CRF polypeptides.

One of skill in the art will recognize that modified CRF polypeptides with CRFR2 antagonist activity can be produced by any of the methods that are well know to those in the art. For example, in certain cases the polypeptide can be expressed and purified from bacterial or insect cells. However, in certain preferred embodiments that polypeptide may be chemically synthesized. This process in particular readily allows the substitution of unnatural and chemically modified amino acids at any given position of the CRF polypeptide.

2. CRFR2 Antibodies and Aptamers

In certain embodiments of the current invention CRFR2 antagonists comprise antibodies that bind to CRFR2. CRFR2 antibodies may comprise polyclonal and/or monoclonal antibodies or fragments thereof. Methods for generating antibodies are well know to those in the art and are detailed below. In general antibodies are raised against an antigen that comprises, at least a portion of the CRFR2 amino acid sequence. Thus it will be understood that antibodies can be raised against the complete CRFR2 amino acid sequence or portions thereof and that the amino acid sequence from any of the CRFR2 protein isoforms (alpha, beta and/or gamma) may be used as the immunogenic antigen. As detailed below CRFR2 derived amino acid sequence may be further coupled to additional amino acid sequences to increase its antigenicity.

In certain cases, CRFR2 antibodies may bind preferentially to certain CRFR2 protein isoforms. In some preferred cases CRFR2 antibodies can be made that bind to only one of the CRFR2 protein isoform. Such antibodies may have the advantage of being able to target specific tissue and/or organs and therefore providing highly specific kinds of CRFR2 antagonists.

Not all antibodies that bind to CRFR2 will act as antagonists thus in many cases the ability of an antibody to block CRFR2 agonism can be tested. Any of the screening assays described to test CRFR2 antagonist activity as described below may be used with respect to CRFR2 antibodies. One specific example of assay to test the antagonist activity of CRFR2 antibodies is shown in FIG. 4b, wherein the anti-CRFR2 IgG is shown to block Ucn 3 agonism of CRFR2. As with other CRFR antagonist antibodies maybe identified that bind CRFR2 but preferentially block certain CRFR agonists. For example, it is contemplated that some CRFR2 antibodies may block Ucn 3 agonism however have little on Ucn 3 agonism. These specific characteristics of certain CRFR2 antibodies may also be identified by the screening assays outlined herein.

In certain further aspects of the invention CRFR2 antibodies may be modified to enhance there efficacy as CRFR2 antagonists. For example, it is preferred that polypeptide therapeutics not illicit an immune response. Thus, in the case where the subject for treatment is a human antibodies may be human antibodies or humanized antibodies, so as to reduce the possibility of immune response. In yet further embodiments, it may be preferred that antibodies be single chain antibodies since the manufacture of single chain antibodies can be substantially stream-lines by production in insect or bacterial expression systems. Thus in certain cases CRFR2 antibodies that act as CRFR2 antagonists may be sequenced and the sequence used to generate single chain antibodies.

It is additionally contemplated that nucleic acid aptamers that bind to CRFR2 may be used to antagonize CRFR2 activity. Methods for selecting aptamers by using recombinant CRFR2 or fragments thereof to purify nucleic acid aptamers from a library, are well known in the art. The technique known as SELEX and can also be automated to enhance the speed and efficacy of selection, for example see U.S. Pat. Nos. 6,569,620 and 6,716,580. Aptamers identified to bind to CRFR2 can then be screened for the ability to antagonize CRFR2, for example by the methods described below. As with other CRFR2 binding molecules it aptamers may be selected for preferential binding to specific CRFR2 protein isoforms. In some specific cases, aptamers may be negatively selected using one CRFR2 protein isoform and then positively selected using a different CRFR2 protein isoform in order to identify aptamers that specifically bind to particular CRFR2 protein isoforms. As used throughout the specification, "positive selection" means collecting molecules that bind to particular target, while "negative selection" means collecting molecules that do not bind to a particular target. Aptamers according to this aspect of the invention may be DNA or RNA, and preferable comprise modified nucleotides that inhibit degradation thereby enhancing activity.

Methods for synthesizing and purifying nucleic acids, such as CRFR2 binding aptamers are well known to those in the art. For example DNA apatamers may be synthesized by PCR, while RNA aptamers can generated by in vitro transcription. In preferred embodiments large scale preparation of aptamers may be accomplished by chemical synthesis, this method allows for DNA, RNA and chemically modified oligonucleotides to incorporated into to the specific aptamer sequence.

3. CRFR2 Interacting Small Molecules

In some aspects of the invention CRFR2 antagonist may be small molecules that bind to CRFR2 and reduce or inhibit its activation. In this embodiment molecules can be identified that bind to CRFR2 such as by the structural methods described in U.S. application Ser. No. 11/199,821 or experimentally by screening a small molecule library for molecules that interact with CRFR2. Once interacting molecules are identified their ability to act CRFR2 antagonists can be assessed by any of the screening methods detailed below. Small molecule CRFR2 antagonist may be preferred in some case since they may be delivered to subjects via a variety of routes, and in some cases may be administered orally.

As discussed above in certain embodiments preferred small molecule CRFR2 antagonists will have a high affinity for CRFR2 than for CRFR1. Thus, in some aspects small molecules may be screened for the ability to bind to CRFR2 with high affinity while not having high affinity for CRFR1. For example, such a screening assays may involve first selecting molecules that do not bind with high affinity to CRFR1, for example by passing the library over a column comprising the CRFR1 ligand binging domain and collecting the molecules that remain unbound (i.e. negative selection). Then these molecules are passed over a column comprising the CRFR2 ligand binding domain and the molecules that bind CRFR2 with high affinity are collected and identified. Many methods are available that can be used for identifying small molecules that bind to CRFR2, for example nuclear magnetic resonance (NMR) analysis and mass spectroscopy. Finally, these molecules can be assessed for their activity as CRFR2 antagonists. CRFR2 specific antagonists may have the advantage of producing fewer side effects since they will not perturb the CRFR1 signaling pathway and thus their effects by be localized to specific organs and tissues of interest.

Similarly, it is contemplated that certain small molecules may antagonize specific CRFR2 protein isoforms. Thus, in certain aspects small molecules may be selected for their, binding to and antagonism of specific CRFR2 isoforms. In this respect the isoform that that is the preferred antagonist target is used to screen for the small molecule in the library. Thus, in certain embodiments certain CRFR2 protein isoforms can be used for negative selection (i.e. to remove small molecules to which they bind) prior to positive selection with the target CRFR2 protein isoform. As described below, the pool of molecules from this selection strategy can then be assessed for activity as an antagonist of the CRFR2 pathway. These isoform specific CRFR2 antagonists may provide further specific targeting of tissues and organs of interest and thus may have improved efficacy and reduced side effects as compared to broad range CRFR2 antagonists.

It is also contemplated that certain small molecule CRFR2 antagonists may bind to CRFR2 however only block agonism of a specific CRFR2 agonist. For example in some aspects a small molecule CRFR2 antagonist may, for example prevent Ucn 2 binding to CRFR2, but have little effect on Ucn 3 binding. Such an antagonist may be used for example to increase the insulin-sensitivity of skeletal muscle cells, while having little effect on beta cell insulin secretion. Conversely a CRFR2 antagonist that reduces Ucn 3 agonism but has little effect on Ucn 2 agonist might be used to reduce insulin secretion from beta cells while having little effect on insulin-sensitivity. Small molecules such as these may be identified by the screening methods described herein since the effect of the molecule on Ucn 2 agonism in muscle cells and Ucn 2 agonism in beta cells can both be assessed. Thus, in certain aspects small molecule CRFR2 antagonists may reduce agonism only with respect to certain agonists.

Production and purification of small molecule CRFR2 antagonists will depend upon the specific molecule, but typically can be accomplished by means of chemical synthesis of by purifying the molecule from a natural source such as plant extract. Methods to achieve substantially pure small molecule synthesis and/or purification are well within knowledge of those skilled in the art. Some exemplary methods that include but are not limited to solvent extraction and chromatographic separation.

4. CRFR2 Agonist Binding Molecules

In certain aspects of the invention CRFR2 antagonists may bind to CRFR2 agonists and reduce or inhibit their ability to bind to or activate CRFR2. These CRFR2 agonist binding molecules may be polypeptides, nucleic acid aptamers or small molecules. In each case the agonist binding molecules must both bind to a CRFR2 agonist and inhibit its ability to agonize CRFR2. In some aspects agonist binding molecules inhibit the interaction of the agonist with CRFR2, however they may also inhibit activation of CRFR2 upon binder or even target the agonist for destruction thereby reducing CRFR2 agonism. In general preferred molecules that act as CRFR2 antagonists will bind to Ucn 2 and/or Ucn 3.

It is contemplated that in certain aspects of the invention CRFR2 antagonists may be Ucn 2 and/or Ucn 3 specific antibodies. Such antibodies may be made by any other methods that are well known in the art, and may be polyclonal antibodies, monoclonal antibodies or fragments thereof. Not all antibodies to Ucn 2 or Ucn 3 will act as CRFR2 antagonists each specific candidate antibodies must be tested for their ability to block CRFR2 agonism by Ucn 2 an/or Ucn 3. Screening assays described below exemplify some of the methods that may be used for testing specific antibodies. Such assays may also be used to determine if a given antibody inhibits agonism of Ucn 2, Ucn 3 or both. In some embodiments of the invention, it is preferable that an antibody have the ability to block both Ucn 2 and Ucn 3 agonism, and such antibodies can be identified by the screening methods provided herein alternatively such antibodies can be made by conjugating Ucn 2 and Ucn 3 specific antibodies.

In certain further aspects of the invention Ucn 2 and/or Ucn 3 antibodies may be modified to enhance there efficacy as CRFR2 antagonists. For example, it is preferred that polypeptide therapeutics not illicit an immune response. Thus, in the case where the subject for treatment is a human antibodies may be human antibodies or humanized antibodies, so as to reduce the possibility of immune response. In certain other embodiments it may be preferred that antibodies be single chain antibodies since the manufacture of single chain antibodies can be substantially stream-lines by production in insect or bacterial expression systems. Thus in certain cases Ucn 2 and/or Ucn 3 antibodies that act as CRFR2 antagonists may be sequenced and the sequence used to generate single chain antibodies.

In certain further aspects of the invention polypeptides that bind to CRFR2 agonists and block their activity may also comprise soluble CRFR ligand binding domains. For example the extra cellular domain of CRFR2 may be used as CRFR2 antagonist since it will bind to and block the activity of Ucn 2 and Ucn 3. Soluble CRFR2 polypeptides may be modified by deletion of amino acids, insertion of amino acids, substitution of amino acids, or by chemical modification so as to enhance its activity as a CRFR2 antagonist or enhance its pharmacokinetics. The activity of such modified polypeptide may be assessed, in for example, the screening assays described below. It is additionally contemplated that the extra cellular domains of various CRFR2 protein isoforms (alpha, beta and/or gamma) may be used as more specific CRFR2 antagonists. For example soluble CRFR2 alpha would be expected to act as a more specific antagonist of CRFR2 alpha than of other CRFR2 protein isoforms and thus may be used to provide tissue or organ specific CRFR2 antagonism.

In certain further aspects of the invention involve small molecules that bind to CRFR2 agonists and act as a CRFR2 antagonists can be identified. It is contemplated that these kinds of small molecule CRFR2 antagonists can be selected from a library based upon binding to a CRFR2 agonists such as Ucn 2 or Ucn 3. Molecules that bind to one or both of the agonists can then be screened for the ability to inhibit Ucn 2 and/or Ucn 3 activity by methods described herein. As with other CRFR2 antagonists certain molecules may have the ability to block agonism Ucn 2 or Ucn 3 specifically. In some cases preferred small molecules will bind to and inhibit the activity of both Ucn 2 and Ucn 3 thereby acting to both decrease insulin load and increase insulin-sensitivity. Thus in certain cases small molecules may be selected for the ability to bind to both Ucn 2 and Ucn 3, and further screened for the ability to block agonism mediated by both molecules.

Finally is also contemplated that nucleic acid aptamers may be used to bind CRFR2 agonists and thereby antagonize CRFR2 activity. Methods for selecting aptamers that bind to nucleic acid moieties are well known to those in the art and can be automated to enhance the speed and efficacy of selection, see U.S. Pat. Nos. 6,569,620 and 6,716,580. Aptamer identified to bind to a CRFR2 agonist, such as Ucn 2 or Ucn 3 are then screening for their ability to antagonize CRFR2 by any method available in the art, for example those described below. Aptamers according to this aspect of the invention may be DNA or RNA, and preferable comprise modified nucleotides that inhibit degradation thereby enhancing activity.

As previously discussed with respect to other embodiments of the instant invention methods for producing and purifying antibodies, small molecules and aptamers are well known to those of skill in the art, and any of these methods may be used to produce CRFR2 agonist binging molecules according to the current invention.

5. Reduction of CRFR2 and/or CRFR2 Agonist Expression

In certain aspects of the invention CRFR2 signaling may be reduced or inhibited by reducing the expression of CRFR2, or to reduce the expression of a CRFR2 agonist such as Ucn 3 and/or Ucn 2. In certain aspects this can be accomplished by administration of a siNA that reduces the expression of one or more of the these polypeptides. Thus in certain aspects of the invention compositions that reduce CRFR2 antagonism will comprise siNAs directed to CRFR2, Ucn 2 and/or Ucn 3. "siNA", as used herein, is defined as a short interfering nucleic acid. Examples of siNA include but are not limited to RNAi, double-stranded RNA, miRNA and siRNA. A siNA can inhibit the transcription of a gene in a cell, mediate degradation of an mRNA in a cell and/or inhibit the translation of a polypeptide fro a mRNA. Typically a siNA may be from 16 to 1000 or more nucleotides long, and in certain embodiments from 18 to 100 nucleotides long. In certain embodiments, the siNA may be 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides long. The siNA may comprise a nucleic acid and/or a nucleic acid analog. Typically, a siNA will inhibit the expression of a single gene within a cell; however, in certain embodiments, a siNA will inhibit the expression of more than one gene within a cell.

Within a siNA, a nucleic acids do not have to be of the same type (e.g., a siNA may comprise a nucleotide and a nucleic acid analog). siNA form a double-stranded structure; the double-stranded structure may result from two separate nucleic acid molecules that are partially or completely complementary. In certain embodiments of the present invention, the siNA may comprise only a single nucleic acid or nucleic acid analog and form a double-stranded structure by complementing with itself (e.g., forming a hairpin loop). The double-stranded structure of the siNA may comprise 16 to 500 or more contiguous nucleobases. The siNA may comprise 17 to 35 contiguous nucleobases, more preferably 18 to 30 contiguous nucleobases, more preferably 19 to 25 nucleobases, more preferably 20 to 23 contiguous nucleobases, or 20 to 22 contiguous nucleobases, or 21 contiguous nucleobases that hybridize with a complementary nucleic acid (which may be another part of the same nucleic acid or a separate complementary nucleic acid) to form a double-stranded structure. siNA (e.g., siRNA) are well known in the art. For example, siRNA and double-stranded RNA have been described in U.S. Pat. Nos. 6,506,559 and 6,573,099, as well as in U.S. Applications 2003/0051263 (now U.S. Pat. No. 7,560,438), 2003/0055020 (now U.S. Pat. No. 7,622,633), 2004/0265839 (now U.S. Pat. No. 7,282,564), 2002/0168707 (now U.S. Pat. No. 6,573,099), 2003/0159161, 2004/0064842, all of which are herein incorporated by reference in their entirety.

In certain aspects of the current invention siNA molecules may also be expressed in cells from an expression vector. For example expression can be under the transcriptional control of a RNA Polymerase III promoter, such as the U6 promoter. Such promoters are preferred for the expression of short RNA sequences such as siRNA molecules. In certain aspects of the invention tissue specific promoters may also be employed, for example promoter that express nucleic acids in pancreatic islet cells, or in skeletal muscle cells. Specific vectors to express siNAs are well known in the art. For example the commercially available pSUPER RNAi System™ available from OilgoEngine® and the pSilencer™ siRNA expression vectors available from Ambion®.

Some specific siNA molecules contemplated for use according to the current invention include but are not limited to siNA molecules that comprise 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more nucleotides that are complementary to the nucleotide sequence encoding human CRFR2 (SEQ ID NO:7), human Ucn 2 (SEQ ID NO:5) and/or human Ucn 3 (SEQ ID NO:6). In some specific cases siNA molecules may be directed to sequences that are unique to a specific CRFR2 isoform (i.e. alpha, beta or gamma). Thus, in certain cases the expression of specific CRFR2 isoforms may be reduced. siNA according to this embodiments may be preferred since they can allow organ or tissue specific CRFR2 antagonism.

Nucleotide molecules for use as siNA CRFR2 antagonists can be prepared and purified by any of the methods that are well known in the art, for example see Sambrook et al., 2001. Likewise methods for delivering siNA molecules into cells are also well known in the art. For example siNAs or siNA expression vectors may be delivered in liposomes such as 1,2-bis(oleoyloxy)-3-(trimethyl ammonio)propane (DOTAP) and cholesterol liposomes or cationic liposomes, see U.S. Pat. No. 6,806,084. Additionally in the case of siNA expression vectors delivery may be accomplished in viral vectors. Some non-limiting examples of viruses contemplated herein for nucleic acid delivery include herpesviaral vectors; adenoviral vectors, such as those described by Karlsson et al., (1986) or derivatives thereof, retroviral and lentiviral vectors, such as those described in U.S. Patent App. 20050014166 (now abandoned); and adeno-associated viral vectors, for example as described in U.S. Pat. No. 5,139,941 and U.S. Pat. No. 4,797,368.

II. Screening Assays to Assess CRFR2 Antagonism

In certain aspects of the invention methods are provided to screen for CRFR2 antagonist activity. Methods for identifying candidate CRFR2 antagonists are detailed above and described in detail in U.S. patent application Ser. No. 11/199,821, incorporated herein by reference. In vitro methods may be used to test whether candidate CRFR2 antagonists are able to block agonism by Ucn 2, Ucn 3 or both molecules. As discussed above in certain cases antagonists may be used that block only Ucn 2 or only Ucn 3. However, in certain other embodiments antagonists that are able to block agonism by both Ucn 2 and Ucn 3 may be identified. The methods below exemplify some of the screening methods that may be used to identify and characterize CRFR2 antagonists.

1. In Vitro Screening for CRFR2 Antagonists

In certain cases methods according to current invention involve in vitro screening methods for characterizing CRFR2 antagonist activity. In general, methods according to these embodiments will involve cell culture systems where the cells express CRFR2. The cells are then treated with a candidate CRFR2 antagonist and the effect of the of the CRFR2 antagonist is assessed by comparing the treated cells with untreated cells. Methods such as this will be of particular use in the case where the cells additionally express a CRFR2 agonist (i.e. wherein there is autocrine regulatory mechanism). On the other hand, methods may also involve administering a CRFR2 agonist or a CRFR2 agonist plus a candidate CRFR2 antagonist and determining the effects of the two treatments on the cells. In certain additional embodiments cells may be treated with additional molecules prior to measuring the effects for CRFR2 antagonist activity, for example cells may be treated with high glucose or with insulin.

A variety of methods may be used to assess the activity of candidate CRFR2 antagonist on cells. Some exemplary methods include, measuring glucose transport, insulin secretion, glucagon secretion, and/or protein phosphorylation. In these methods a candidate CRFR2 antagonist may be administered to the cells. For example the candidate can be administered before, concurrently with or after administration of a CRFR2 agonist. As previous described by Rivier et al. 2002, certain CRFR2 antagonists must be administered prior to agonist administration (Antisauvagine-30) while other are active when administered concurrently with the CRFR2 agonist (astressin2B). In certain further embodiments a candidate CRFR2 antagonist may be applied to the CRFR2 agonist prior to administering the mixture to the cells. This method may be of particular use wherein the candidate CRFR2 antagonist is a molecule that binds to a CRFR2 agonist, such as an antibody or an aptamer. These general methods provide both a qualitative and quantitative way to measure CRFR2 antagonist activity, and also provide methods for measuring the activity of antagonists with respect to individual CRFR2 agonist, for example Ucn 2 and/or Ucn 3.

Ucn 2 Effects on Myotubes

Figure 3:
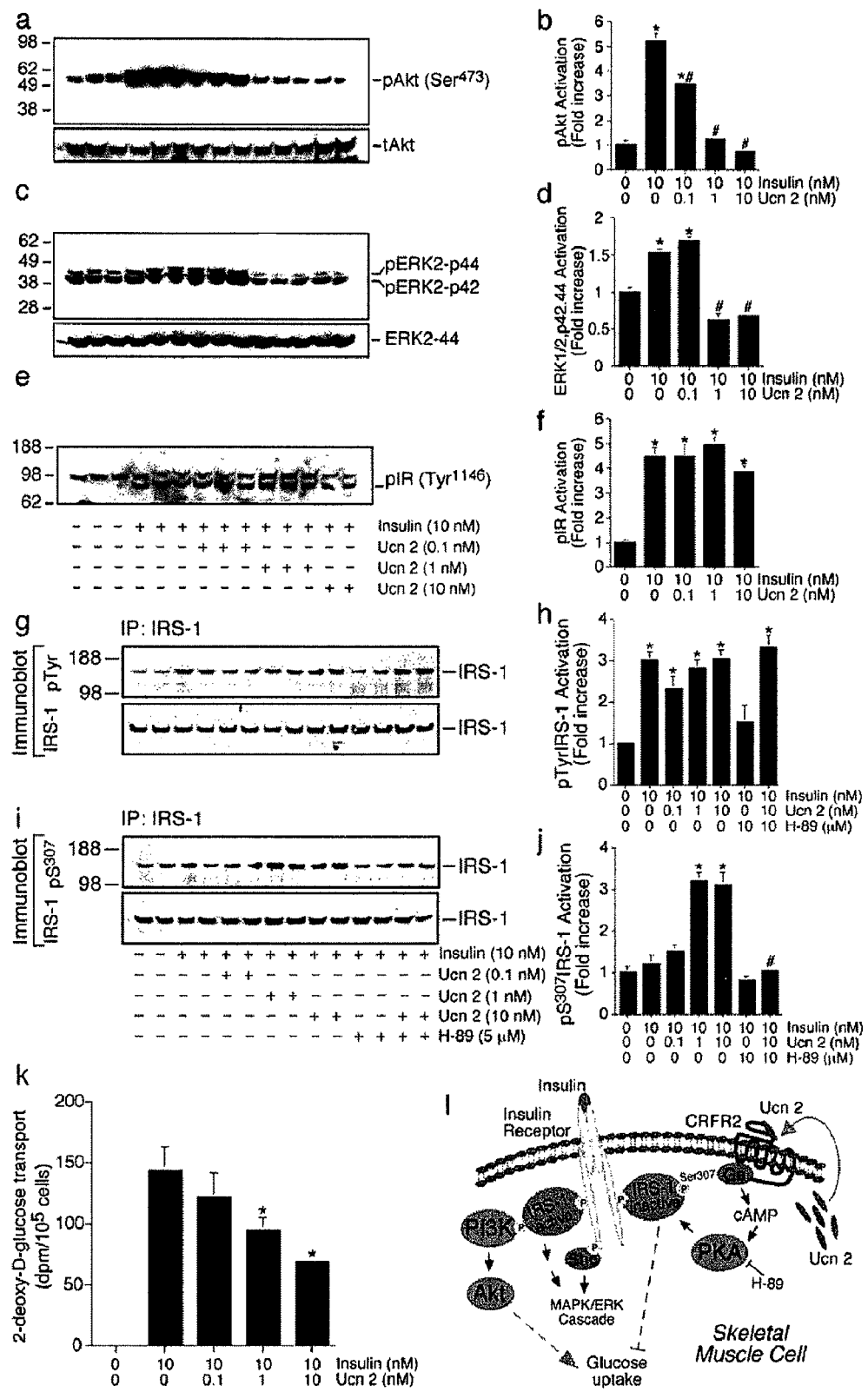
FIG. 3a-l: Urocortin 2 effects on muscle glucose uptake are mediated by inhibition of insulin signaling. (a-f). Ucn 2 inhibits the insulin-induced Akt and ERK1/2 phosphorylation but not the insulin receptor phosphorylation. Differentiated C2C12 myotubes were pre-incubated with or without Ucn 2 peptide (0.1, 1 or 10 nM) for 1 hour prior to insulin treatment (10 nM, 5 min). Cell lystates were resolved using 4-12% gradient polyacrylamide gels. Gels were electrophorectically transferred to membranes and probed with antibodies specific for the phospho proteins pAkt (Ser 473), pERK1/2 or pIR (Tyr1146). Stimulation of Akt, ERK or insulin receptor (IR) activation was calculated by fold activation of the phosphorylated form normalized to total and compared with the untreated controls (a, d and f, graphs). Ucn 2 dose dependently inhibits the insulin-induced phosphorylation of Akt (a and b) and ERK1/2 (c and d) but not the IR (e and f). (g-j) Ucn 2 treatment increases the phosphorylation of serine residue 307 and not the tyrosin phosphorylation of IRS-1. Myotube cells, treated with or without PKA inhibitor (H-89), were incubated with insulin and different concentrations of Ucn 2. IRS-1 immunoprecipitated proteins were electrophoresed as before and the immunoblots were probed for phosphorylated tyrosin (g), phosphorylated serine 307 IRS-1 (i) and total IRS-1 (g, i). The tyrosine phosphorylation of IRS-1 in response to insulin treatment remains unchanged following Ucn 2 treatment (g, h). In contrast, Ucn 2 strongly increases the phosphorylation of IRS-1 on serine residue 307 (i, j). The phosphorylation of IRS-1 on S307 by Ucn 2 was completely blocked by pretreatment with the PKA inhibitor H-89 (i, j). (k) The effect of Ucn 2 on [$^3$H]2-deoxy-D-glucose uptake in differentiated C2C12 myotubes. Cells were incubated for 2 hours in low glucose, serum free medium and treated with Ucn 2 (0.1, 1 or 10 nM) or without (control) for 30 min prior to insulin administration (10 nM). Glucose uptake was measured 5 min following exposure to [$^3$H]2-deoxy-D-glucose. Non-specific uptake was measured by incubating muscle tissue with cytochalasin B, which binds to the glucose uptake transporter (GLUT) and inhibits glucose transport into the cell. Specific uptake was calculated by subtracting non specific from total glucose. (l) Schematic representation of the putative cellular mechanisms mediating the effect of Ucn 2 and CRFR2 on the insulin signaling and glucose uptake in skeletal muscle cells. * indicates p<0.05 vs. no treatment. # indicates p<0.05 vs. insulin treatment (b, d, f) or p<0.05 vs. insulin treatment and Ucn 2 (i).

In certain aspects of the invention CRFR2 antagonists may be identified by determining their effectiveness in blocking Ucn 2 activity in myotubes. For example, as shown in FIG. 3, Ucn 2 reduces Akt and ERK phosphorylation as well as glucose transport in insulin treated myotubes. Thus, candidate CRFR2 antagonists can be tested for their ability to block these Ucn 2 mediated effects. These methods involve culturing myotubes and stimulating the cells with insulin, insulin plus Ucn 2 or insulin plus Ucn 2 plus a candidate CRFR2 antagonist. The CRFR2 antagonist activity may then be measure by its ability to reverse or partially reverse the effects of Ucn 2 plus insulin treatment as compared to the insulin treatment alone. The effects of Ucn 2 treatment can be assessed in number of ways for example the phosphorylation of Akt or ERK may be measured or glucose uptake by the myotubes may be measured. Thus, a CRFR2 antagonist can be defined as having the ability to increase Akt or ERK phosphorylation in the presence of insulin and Ucn 2. On the other hand a CRFR2 antagonist may be defined as a molecule that increases glucose uptake in myotubes in the presence of insulin and Ucn 2. The foregoing methods may be used, in some instances to characterize a CRFR2 antagonist and in some specific cases may be used to identify a CRFR2 antagonist that functions to block Ucn 2 agonism.

Ucn 3 Effects on Islet Cells

In certain aspects of the invention, CRFR2 antagonists may be identified by determining their ability to block the effects of Ucn 3 in islet cells. Since islet cells express Ucn 3 isolated islet are cultured in the presence of low glucose, high glucose and high glucose plus a candidate CRFR2 antagonist. CRFR2 antagonist activity can then be measured by determine the glucose secretion of the islet cells. In this respect, a CRFR2 antagonist can be defined as a molecule that inhibits insulin secretion of islet cells under conditions of high glucose. For certain application an assay such as this may be used to determine the effectiveness of a candidate CRFR2 antagonist in blocking Ucn 3 specific agonism. FIG. 4b depicts to results of this type of assay and identifies an anti-Ucn 3 IgG preparation that can act as a CRFR2 antagonist, while FIG. 4a shows that astressin$_2$B has CRFR2 antagonist activity as well.

2. In Vivo Screening for CRFR2 Antagonists

In vivo animal models may also be used to screen for CRFR2 antagonists. In these aspects an animal model wherein the animal displays chronically elevated serum insulin and/or insulin resistance may be used. The animal is administer the candidate CRFR2 antagonist for a period of time after which the metabolic profile of the treated animal is compared to a control animal. For the purposes of these experiments "comparing a metabolic profile" can comprises comparing serum glucose levels, serum insulin levels, response to a glucose tolerance test, response to an insulin tolerance test, percentage lean body mass and/or accumulation of liver triglycerides. Methods for comparing any of these metabolic markers are well known in the art and described in detail in the examples section.

The Effect of CRFR2 Antagonism on Mice Fed a High Fat Diet

Mice fed a high fat diet (45% kcal from fat) versus mice on a standard diet (11% kcal from fat) are an excellent model for testing CRFR2 antagonist. Mice are fed the indicated diet for a period of 16 weeks after which the mice exhibit elevated serum glucose and insulin levels and display insulin resistance. In one example these mice may be injected with glucose or glucose and a candidate CRFR2 antagonist (in a glucose tolerance test as described below). The serum glucose level of the mice are then assessed over a time period. In this respect a CRFR2 antagonist can be defined by it ability to shorten the time period required for serum glucose levels to return to normal after injection. FIG. 1c depicts such a screening method wherein it is demonstrated that astressin$_2$B has CRFR2 antagonist activity. A similar assay may be performed with mice on a high fat diet wherein the mice are injected with insulin or insulin plus a CRFR2 antagonist and serum glucose levels are monitored over a period of time (as in an insulin tolerance test as detailed below). In this respect a CRFR2 antagonist can be identified by its ability to increase the rate at which serum glucose is reduced.

III. Methods for Producing Antibodies

As described above certain aspects of the invention involve to use of antibodies that act as CRFR2 antagonists. Antibodies may be made by any of the methods that as well known to those of skill in the art. The following methods exemplify some of the most common antibody production methods.

1. Polyclonal Antibodies

Polyclonal antibodies generally are raised in animals by multiple subcutaneous (sc) or intraperitoneal (ip) injections of the antigen. As used herein the term "antigen" refers to any polypeptide that will be used in the production of a antibodies. Antigens for use according to the instant invention include CRFR2, Ucn 2, Ucn 3, polypeptides or fragments of any of the foregoing. Some very specific examples are the antibodies that bind to Ucn 3, exemplified herein, that may be generating by immunizing an animal with human Gly-Tyr-Ucn 3 that ahs been chemically conjugated to antigenic polypeptide. Furthermore in certain cases, it is preferable to generate antibodies that are selective for a specific CRFR2 protein isoform by using isoform specific polypeptide sequence as the antigen. Thus in certain cases, amino acid sequences according to SEQ ID NO:26, SEQ ID NO:27 or SEQ ID NO:28 may be included in the antigen.

It may be useful to conjugate an antigen or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, SOCl$_2$, or $R^1N=C=NR$, where R and $R^1$ are different alkyl groups.

Animals are immunized against the immunogenic conjugates or derivatives by combining 1 mg of 1 μg of conjugate (for rabbits or mice, respectively) with 3 volumes of Freud's complete adjuvant and injecting the solution intradermally at multiple sites. One month later the animals are boosted with ⅕ to ⅒ the original amount of conjugate in Freud's complete adjuvant by subcutaneous injection at multiple sites. 7 to 14 days later the animals are bled and the serum is assayed for specific antibody titer. Animals are boosted until the titer plateaus. Preferably, the animal boosted with the same antigen conjugate, but conjugated to a different protein and/or through a different cross-linking reagent. Conjugates also can be made in recombinant cell culture as protein fusions. Also, aggregating agents such as alum are used to enhance the immune response.

2. Monoclonal Antibodies

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, monoclonal antibodies of the invention may be made using the hybridoma method first described by Kohler & Milstein (1975), or may be made by recombinant DNA methods (Cabilly et al.; U.S. Pat. No. 4,816,567).

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding 1986).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA.

Culture medium in which hybridoma cells are growing is assayed for production of monoclonal antibodies directed against the target antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard (1980).

After hybridoma cells are identified that produce antibodies of the desired specificity, affinity, and/or activity, the clones may be subcloned by limiting dilution procedures and grown by standard methods, Goding (1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al. (1984), or by covalently joining to the immunoglobulin coding sequence all or part of the coding sequence for a non-immunoglobulin polypeptide. In that manner, "chimeric" or "hybrid" antibodies are prepared that have the binding specificity for any particular antigen described herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for the target antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as 3H, 14C, 32P, 35S, or 125I, a fluorescent or chemiluminescent compound, such as fluorescein isothiocyanate, rhodamine, or luciferin; biotin; radioactive isotopic labels, such as, e.g., 3H, 14C, 32P, 35S, or 125I, or an enzyme, such as alkaline phosphatase, beta-galactosidase or horseradish peroxidase.

Any method known in the art for separately conjugating the antibody to the detectable moiety may be employed, including those methods described by Hunter et al. (1962); David et al. (1974); Pain et al. (1981); and Nygren (1982).

The antibodies of the present invention may be employed in any known assay method, such as competitive binding assays, direct and indirect sandwich assays, and immunoprecipitation assays (Zola, 1987).

Competitive binding assays rely on the ability of a labeled standard (which may be a purified target antigen or an immunologically reactive portion thereof) to compete with the test sample analyte for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

3. Humanized Antibodies

As discussed previously, antibodies for use in the methods of the invention may be polyclonal or monoclonal antibodies or fragments thereof. However, in some aspects it is preferred that the antibodies are humanized such that they do not illicit an immune response in subject being treated. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., 1986); Riechmann et al., 1988; Verhoeyen et al., 1988), by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties, for example the ability to block or reduce CRFR2 signaling. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed Aug. 21, 1992 now U.S. Pat. No. 5,821,337, which is a continuation-in-part of application Ser. No. 07/715,272 filed Jun. 14, 1991, now abandoned.

4. Human Antibodies

Human monoclonal antibodies can be made by the hybridoma method. Human myeloma and mouse-human heteromyeloma cell lines for the production of human monoclonal antibodies have been described, for example, by Kozbor (1984) and Brodeur et al. (1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al. (1993); Jakobovits et al. (1993).

Alternatively, the phage display technology (McCafferty et al., 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle.

Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson et al. (1993). Several sources of V-gene segments can be used for phage display. Clackson et al. (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al. (1991), or Griffith et al. (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This techniques allows the production of antibodies and antibody fragments with affinities in the nM range. A strategy for making very large phage antibody repertoires (also known as "the mother-of-all libraries") has been described by Waterhouse et al. (1993), and the isolation of a high affinity human antibody directly from such large phage library has been reported. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published Apr. 1, 1993). Unlike traditional humanization of rodent antibodies by CDR grafting, this technique provides completely human antibodies, which have no framework or CDR residues of rodent origin.

5. Bispecific Antibodies

Bispecific antibodies are monoclonal, preferably human or humanized, antibodies that have binding specificities for at least two different antigens. For example, bispecific antibodies specifically binding Ucn 2 and Ucn 3 are within the scope of the present invention.

Methods for making bispecific antibodies are known in the art. Traditionally, the recombinant production of bispecific antibodies is based on the coexpression of two immunoglobulin heavy chain-light chain pairs, where the two heavy chains have different specificities (Millstein and Cuello (1983). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published May 13, 1993), and in Traunecker et al. (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in copending application Ser. No. 07/931,811 filed Aug. 17, 1992.

For further details of generating bispecific antibodies see, for example, Suresh et al. (1986).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques. In some aspects heteroconjugate antibodies that bind to Ucn 2 and Ucn 3 and thereby reduce CRFR2 signaling in the pancreas and skeletal muscle are particularly preferred embodiments of the instant invention IV. Conventional Treatment for Insulin Resistance and Combination Therapies A variety of conventional pharmacological treatments for type 2 diabetes are well known in the art (Florence and Yeager, 1999). In some aspects of the invention, one or more of these agents may be administered in combination or in conjunction with compositions according to the invention. Such combination therapy may reduce effective dosage of currently available drugs and thus reduce the side effects associated with therapy regimens. Some specific compounds currently in use comprise; sulfonylureas such as tolbutamide (Orinase) and chlorpropamide; biguanides, such as metformin; alpha-glucosidase inhibitors, such as acarbose and miglitol; thiazolidinediones, such as rosiglitazone, pioglitazone and troglitazone; and repaglinide.

Under certain conditions insulin treatment may be used in conjunction with the methods according to the instant invention. In this case increasing the insulin-sensitivity of an individual prior to or along with insulin administration may lower the effective dosage or frequency at which the insulin need to be administered. For example, under certain circumstances insulin is used in the treatment of subject with insulin resistance. In particular, when a subject is both insulin resistant and has an insulin deficient (e.g. subjects with both type 1 and type 2 diabetes). Methods according to the invention used in conjunction with insulin therapy are high preferred in these cases.

V. Pharmaceutical Preparations

Therapeutics for use in methods of the invention may be formulated into a pharmacologically acceptable format. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one non-charged lipid component comprising a siNA, an antibody or a CRFR2 antagonist active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed., 1990, incorporated herein by reference). A pharmaceutically acceptable carrier is preferably formulated for administration to a human, although in certain embodiments it may be desirable to use a pharmaceutically acceptable carrier that is formulated for administration to a non-human animal, such as a canine, but which would not be acceptable (e.g., due to governmental regulations) for administration to a human. Except insofar as any conventional carrier is incompatible with the active ingredient, its use in the therapeutic or pharmaceutical compositions is contemplated.

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Where clinical application of liposomal compositions containing a siNA (i.e. siNA directed to CRFR2, Ucn 2 or Ucn 3) is undertaken, it will generally be beneficial to prepare the lipid complex as a pharmaceutical composition appropriate for the intended application. This will typically entail preparing a pharmaceutical composition that is essentially free of pyrogens, as well as any other impurities that could be harmful to humans or animals. One may also employ appropriate buffers to render the complex stable and allow for uptake by target cells.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

The therapeutic compositions of the present invention may include classic pharmaceutical preparations. Administration of therapeutic compositions according to the present invention will be via any common route so long as the target tissue is available via that route. For example in the case of antibodies, antibody fragments, or siNA compositions an intravenous route of administration may be preferred. In the case of a small molecule or certain polypeptide inhibitors of CRFR2 signaling routes of administration could additionally include oral routes or even nasal, buccal, rectal, vaginal or topical. Alternatively, administration may be by orthotopic, intradermal subcutaneous, intramuscular, intraperitoneal or intravenous injection. In certain specific cases, compositions according to the current invention maybe administered at there site of actions, such as delivery directly to the skeletal muscle or the pancreas.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired. Thus, in some case dosages can be determined by measuring for example changes in serum insulin or glucose levels of a subject.

Precise amounts of the therapeutic composition may also depend on the judgment of the practitioner and are peculiar to each individual. The amount of a molecule administered will, of course, be dependent on the subject being treated, on the subject's weight, the severity of the affliction, the manner of administration and the judgment of the prescribing physician. Other factors affecting the dose include the physical and clinical state of the patient, the route of administration, the intended goal of treatment (e.g., alleviation of symptoms versus attaining a particular serum insulin or glucose concentration) and the potency, stability and toxicity of the particular therapeutic substance. The therapy may be repeated intermittently while symptoms detectable or even when they are not detectable. The therapy may be provided alone or in combination with other drugs.

For systemic administration, a therapeutically effective dose can be estimated initially from in vitro assays. For example, a dose can be formulated in animal models to achieve a circulating concentration range that includes the $IC_5$ as determined in cell culture. Such information can be used to more accurately determine useful doses in humans.

Initial dosages can also be estimated from in vivo data, e.g., animal models, using techniques known in the art as well as those specifically presented herein. One having ordinary skill in the art could readily optimize administration to humans based on animal data such as the data provided here.

Methods for estimating dose conversions between animal models and humans have previously been developed. In general, these algorithms have been used to extrapolate an animal dose to a dose that would be tolerated by a human. For example, method for dose conversions have previously been disclosed by Freireich et al. (1966). The conversion methods taught by Freireich calculate equivalent doses between species using surface area (m2) rather than mass (kg), a method that correlates much more closely to actual data than body mass conversions. Specifically, Freireich teaches how to use an animal 10% lethal dosage ($LD_{10}$) value to estimate the maximum tolerated doses in a human. Freireich also discussed method for converting a dose in mg/kg to a dose in mg/m2 by using the "km" conversion factor for the given animal. For example, in the case of a laboratory mouse the km is approximately 3.0. Thus, in mice mg/m2=km (3.0 for mice)×dose in mg/kg.

More recent studies regarding species dose scaling have further elaborated upon the methods of Freireich. These newer studies have reduced error associated with conversion between species to determine human tolerable doses. For example, Watanabe et al. (1992) describes that a conversion of doses between species using body surface area may not be the most accurate method per se for predicting a human equivalent dosage. Nonetheless, the scaling factors set forth by Watanabe yield results that are with-in the margin of error of the older Freireich conversions. Currently accepted methods for determining a proper starting dose in humans expand upon the methods set forth by Freireich. For example, Mahmood et al. (2003) provides a discussion regarding the choice of a proper starting dose in humans given dose studies in animals.

Preferably, a therapeutically effective dose of CRFR2 antagonist described herein will provide therapeutic benefit without causing substantial toxicity. Toxicity of the molecules described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975).

EXAMPLES

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of Ucn 2-Null Mice

To determine the physiological role of Ucn 2, mice deficient in this peptide were generated. A genomic DNA clone containing Ucn 2 was isolated and a targeting construct in which the full Ucn 2 coding sequence was replaced with a neomycin-resistant gene cassette was generated. J1 embryonic stem (ES) cells were electroporated with the targeting construct and were selected as previously described (Smith et al., 1998). Targeted ES cells were injected into C57BL/6 mice blastocysts to generate chimeric mice, which transmitted the null mutation through the germline. Germline transmission of the disrupted allele was confirmed by Southern blot analysis. Ucn 2 expression was not detected in knock-out mice by either RT-PCR or immunohistochemistry (methods described below). Mutant mice were found to be fertile and the mutant allele was transmitted in a Mendelian fashion.

RT-PCR Analyses

For semi-quantitative RT-PCR total RNA was extracted from the brain, skeletal muscle and skin of Ucn 2-null mice and wild type littermates and isolated using the Trizol RNA reagent (Molecular Research Center, Cincinnati, Ohio) according to the manufacturer's recommendations. To avoid false positive results caused by DNA contamination, samples were treated with DNase for 30 min at 37° C. using the RQ1 RNase-free DNase (Promega Corp., Madison, Wis.). Semi-quantitative RT-PCR was used to determine the levels of endogenous Ucn 2 present in the tissues studied. For these experiments, the expression of the ribosomal protein S16 served as internal control. The PCR conditions were as follows: cDNA equivalent to 200 ng of total RNA was amplified by PCR™ for 35 cycles at an annealing temperature of 60° C. The final $MgCl_2$ concentration was 3 mM, and each reaction contained 2.5 U of Taq DNA polymerase (BIO-X-ACT DNA polymerase, Bioline UK Ltd., London, UK).

Immunohistochemistry

Adult Ucn 2 null mice and wild type littermates were anesthetized with chloral hydrate (350 mg/kg, ip) and perfused with 4% paraformaldehyde fixative. Frontal 25 μm thick sections throughout the brain were prepared for avidin-biotin-immunoperoxidase localization of Ucn 2 immunoreactivity using Vectastain Elite reagents (Vector Laboratories, Burlingame, Calif.). Rabbit antiserum against mouse Ucn 2, has been previously produced and characterized, was used at a final dilution of 1:4000. Specificity of immunostaining was evaluated using primary antisera preincubated overnight at 4° C. with 0-300 μM synthetic Ucn 2. These experiments confirmed that the mice were phenotypically Ucn 2 null.

Example 2

The Effect of Ucn 2 on the Handling of Glucose Load

The ability of the Ucn 2 null mice and their wild type littermates to handle a glucose or insulin load was assessed using a standard glucose tolerance test (GTT) or insulin tolerance test (ITT) as described below. In separate experiments, mice were injected with saline or Ucn 2 peptide (0.1 μg/kg body weight, IP), 20 min prior to the ITT and GTT, or with astressin 2B (30 μg/kg body weight, IP), 20 min prior to the GTT in order to determine the effect of these molecules on handling of glucose load.

The results of the glucose load tests indicated that glucose tolerance was significantly enhanced in the mutant mice compared with their wild type littermates (FIG. 1a). Administration of synthetic Ucn 2 peptide to mutant mice prior to the glucose tolerance test restored blood glucose to wild type levels (FIG. 1b). Interestingly, administration of the CRFR2 selective antagonist astressin2B (Rivier et al., 2002), to wild type mice results in a glucose tolerance test profile that mirrors that of Ucn 2 null mice (FIG. 1c). Fasting basal and glucose-induced elevated insulin levels were similar in the two groups (FIG. 1d), indicating that enhanced glucose tolerance in Ucn 2 null mice is not due to increased insulin secretion into the bloodstream. Ucn 2-null mice demonstrated increased insulin-sensitivity compared with their wild type littermates as determined using an insulin tolerance test (FIG. 1e). Administration of synthetic Ucn 2 peptide to null mutant mice prior to the insulin tolerance test restored blood glucose levels to those of wild type mice (FIG. 1e). These data indicate that CRFR2 signaling is important for regulating insulin-sensitivity in cells.

GTT

For the purposes of GTT tests, mice were fasted overnight for 14 hour following by intraperitoneal (IP) glucose injection (2 g/kg body weight). Whole venous blood obtained from the tail vein at 0, 15, 30, 60, 90 and 120 min after the injection was measured for glucose using an automatic glucometer (One Touch, Lifescan, Daly). To assess insulin release, glucose (3 g/kg body weight) was injected IP, and blood was collected by retro-orbital eye bleed at 0, 2, 5, 15, and 30 min after the injection, immediately centrifuged, and the plasma stored at −20° C. Insulin levels were measured using a commercially available radioimmunoassay kit (Linco, St. Louis, Mo.).

ITT

For insulin tolerance tests, fasted male mice were injected with insulin (0.75 U/kg body weight, Sigma, St. Louis, Mo.) and blood glucose levels were measured before and at 15, 30, 60 and 90 min following insulin injection.

Example 3

Ucn 2 Expression Modulate Lean Body Mass

Figure 2:
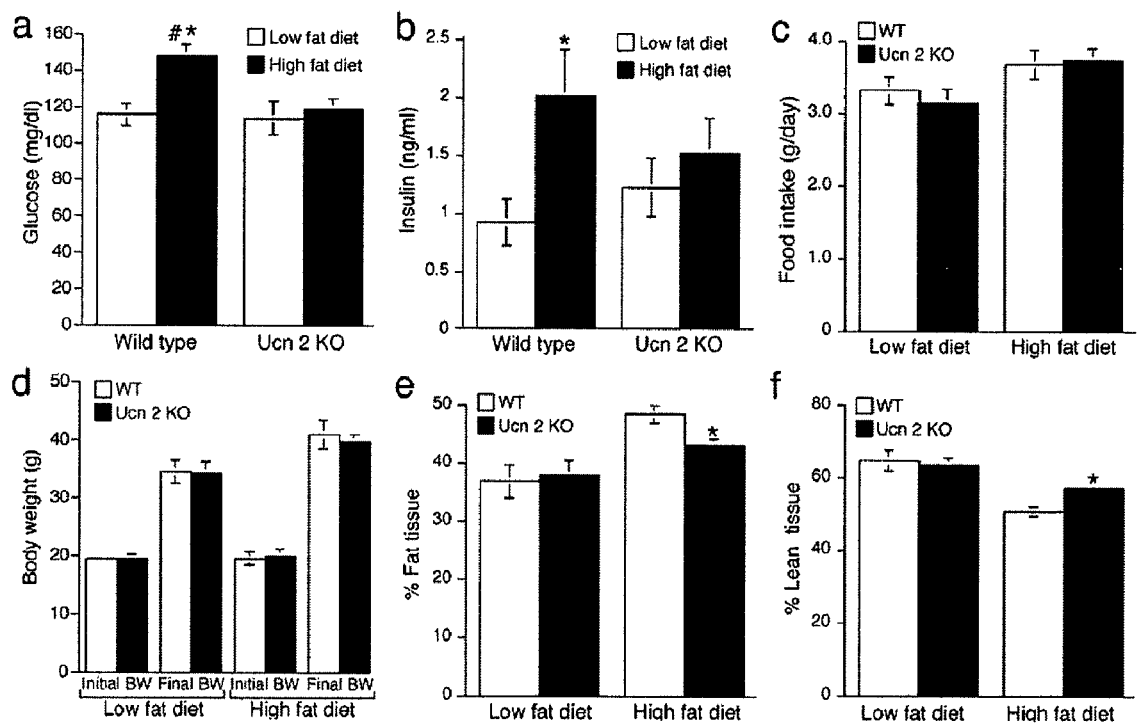
FIG. 2a-f: Ucn 2 null mice placed on a high fat diet exhibit increased insulin-sensitivity and are protected against fat induced insulin resistance. (a-f) Ucn 2 null mice and their wild type littermates were placed on a high fat diet (45% kcal fat) or standard chow diet (10% kcal fat) for 16 weeks. Significant increases in blood glucose (a) and insulin levels (b) were observed only in the wild type mice and not in Ucn 2 null mice. No differences were observed in food intake (c) or body weight (d) between mutant and wild type mice both in the high fat or low fat groups. Body composition of Ucn 2 null mice placed on a high fat diet demonstrate decreases in fat (e) and increases in lean tissue (f) compared to wild type littermates.

Previous studies have shown that mice fed a high-fat diet are an excellent model to study impaired glucose tolerance and ontogeny of type 2 diabetes. To explore glucose metabolism in Ucn 2 null mice, mutant and wild type mice were placed on a high fat (45% kcal from fat) or a standard chow diet (11% kcal from fat) for 16 weeks (FIG. 2 a-f). Following the each treatment the body composition of the mice was determined by dual-energy X-ray absorptiometry (DXA) as described below. Data from the body composition experiments were analyzed to determine fat and lean tissue masses and bone mineral content and density. Ucn 2-null mice and wild type mice gained weight (FIG. 2d) and consumed food (FIG. 2c) similarly, both on a standard diets and when fed high fat diets. Remarkably, however, significant increases in blood glucose (FIG. 2a) and insulin levels (FIG. 2b) were observed only in the wild type mice and not in Ucn 2 null mice. Interestingly, however DXA analysis of the Ucn 2 null mice placed on a high fat diet demonstrated decreased fat (FIG. 2e) and increased lean tissue (FIG. 2f) in these mice as compared to wild type littermates. These data indicated CRFR2 antagonism may be exploited to reduce weight gain and/or increase lean tissue mass.

DXA

DXA measurements were conducted using the GE-Lunar PIXImus as previously described and validated (Nagy and Clair, 2000). The head of the animal was excluded from the analysis using the exclusion tool provided with the software as previously described (Nagy and Clair, 2000).

Example 4

Mechanism of Ucn 2 Action

Figure 4:
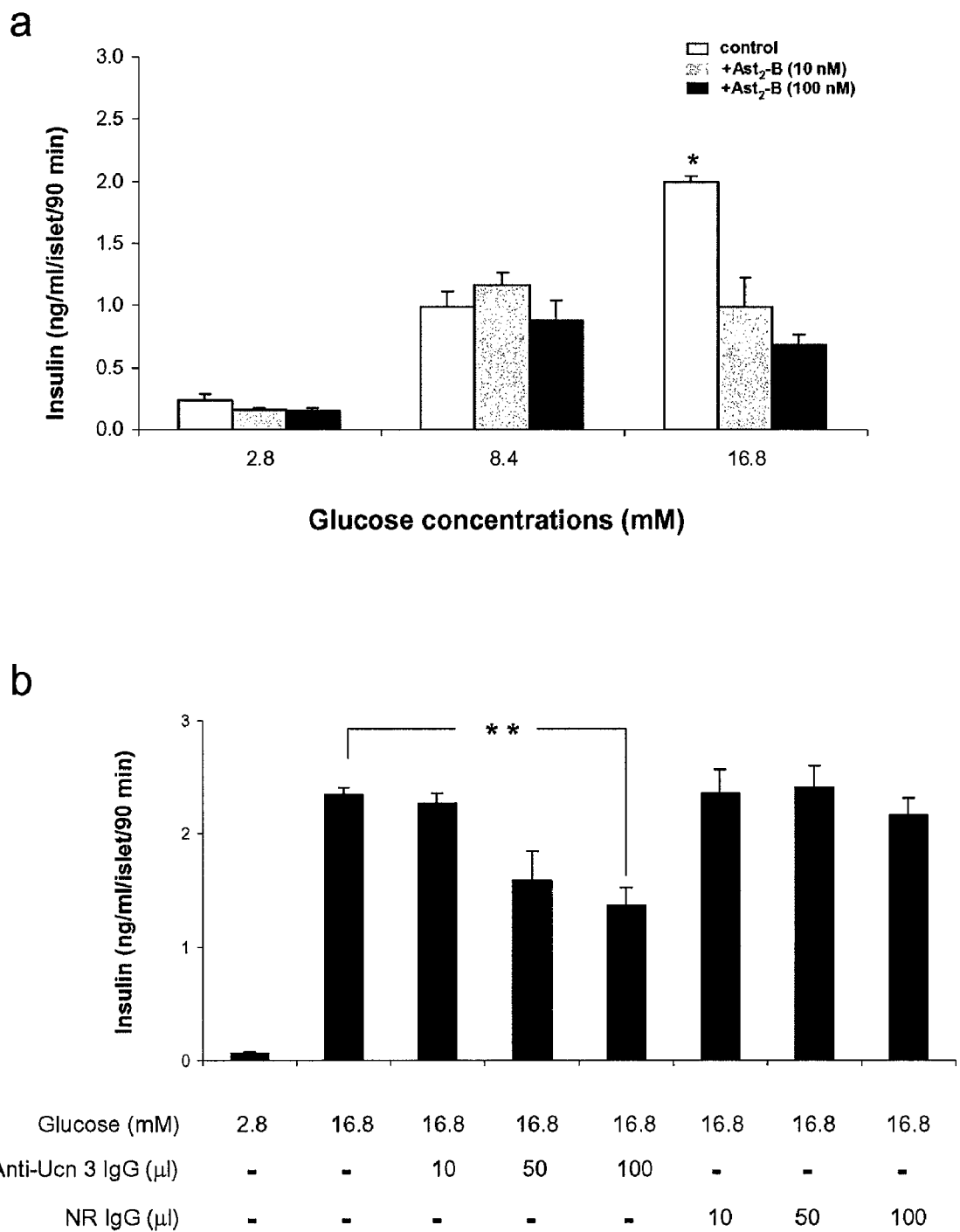
FIG. 4a-b: The effect of CRFR2 antagonist on insulin secretion in isolated rat islets. (a) The effect of astressin2B (Ast2-B) on insulin secretion in response to glucose in isolated rat islets. X-axis indicates the concentration of insulin secreted by islets over period of 90 minutes. Y-axis indicates the concentration of glucose (mM) used to stimulate the islets. The asterisk indicates a statistically significant difference between results from the control versus Ast2-B. (b) Isolated rat isles were pre-treated with anti-Ucn 3 IgG or control IgG followed by addition of indicated concentration of glucose. Y-axis indicates insulin secretion from the treated islets. The double asterisks indicate a statistically significant difference between the indicated treatments.

To explore the cellular mechanisms mediating the effect of Ucn 2 on glucose transport in skeletal muscle, the effects of Ucn 2 on insulin signaling in C2C12 myotubes were studied. Studies indicated that Ucn 2 inhibits the insulin-induced phosphorylation of Akt in a dose dependent fashion (FIG. 3 a,b). The inhibitory effect of Ucn 2 and the CRFR2 activation on insulin receptor signaling may be mediated early in the signaling cascade since ERK1/2 phosphorylation following insulin stimulation is also inhibited by Ucn 2 treatment (FIG. 3 c,d). However, no significant differences in the insulin-induced phosphorylation of the insulin receptor were observed following Ucn 2 treatment (FIG. 3 e,f). The inhibition of insulin signaling by Ucn 2 is also reflected in the insulin induced glucose uptake in C2C12 myotubes, which is dose dependently inhibited by Ucn 2 (FIG. 4 k). These results indicate that Ucn 2 inhibits interactions between the insulin signaling pathway components.

The forgoing results may suggest that Ucn 2 inhibits interactions between the insulin signaling pathway components that occur with regards to the functions of the insulin receptor substrate 1 (IRS-1). IRS-1 plays a critical role in insulin signaling. In response to insulin, IRS-1 becomes tyrosine phosphorylated and recruits a number of SH2 containing signal transducers including PI 3-kinase. While the phosphorylation of IRS-1 on tyrosine residue is required for insulin-stimulated responses, the phosphorylation of IRS-1 on several serine residues, especially serine residue 307, act to terminate the insulin effects (see Gaul et al., 2005). A delicate balance between "positive" IRS-1 tyrosine phosphorylation vs. "negative" IRS-1 serine phosphorylation may regulate the IRS-1 functions (Gaul et al., 2005). In order to further explore the molecular mechanisms mediating the effect of Ucn 2 and CRFR2 on insulin signaling in skeletal muscle, the effects of Ucn 2 on the IRS-1 phosphorylation were investigated. Results of these studies demonstrate that tyrosine phosphorylation of IRS-1 in response to insulin treatment remain unchanged following Ucn 2 treatment (FIG. 3 g,h). In contrast, Ucn 2 greatly increases the phosphorylation of IRS-1 on serine residue 307 (FIG. 3 i,j). Phosphorylation of IRS-1 on S307 may induce a conformational change in IRS-1 that reduces its affinity for the insulin receptor (Aguirre et al, 2000). CRFR2 signaling leads to, among other things, the stimulation of adenylyl cyclase and activation of protein kinase A (PKA) (Perrin and Vale, 1999). The phosphorylation of IRS-1 on S307 by Ucn 2 was completely blocked by pretreatment with the PKA inhibitor H-89 (FIG. 3 i,j). Thus, it appears that in skeletal muscle cells Ucn 2, through its cognate type 2 CRF receptor, can modulate insulin signaling and glucose uptake by activating the cAMP/PKA signaling, which in turn will phosphorylate the IRS-1 on S307 (FIG. 3 l). Phosphorylation of IRS-1 on S307 will drive the IRS-1 toward an inactive state, thereby reducing insulin signaling (FIG. 3 l).

Culture Conditions and Glucose Uptake in C2C12 Myotubes

For these analyses C2C12 myoblasts were cultured in Dulbecco's modified Eagles medium (DMEM) supplemented with 10% fetal bovine serum and 1% (v/v) antibiotic solution at 37° C. in a 5% CO2-humidified atmosphere. When subconfluent density was achieved, cells were transferred to differentiation media containing 2% horse serum for 8 to 10 days in which time the myoblast cells were fully differentiated to functional myotubes. The C2C12 myotubes were washed once with serum free DMEM and were transferred to low glucose serum free DMEM containing 0.1% BSA for two hours. After starvation cells were washed with Hank's balanced saline solution (HBSS) and incubated with the same buffer for an additional two hours. To determine the effect of Ucn 2 on insulin-induced glucose uptake, 30 min incubation in HBSS without or with increasing concentrations (0.1, 1 or 10 nM) of Ucn 2 was carried out. Insulin was added at 10 nM concentration directly into the HBSS and incubation continued for additional 30 min. The reaction was performed by adding a mixture of [3H]2-DG (0.2 µCi/ml) and non-radioactive 2-DG (final concentration 0.1 mM) for 5 min. The solution was removed by suction and the cells rapidly washed four times with ice-cold PBS. Radiolabel glucose was released from the cells by incubating the cells with 1N NaOH for 30 min. An aliquot for protein assay was taking before neutralizing the sample with 1N HCl. The extract was counted for radioactivity in EcoLume scintillation fluid using a beta counter. Non-specific uptake was measured by incubating the cells with cytochalasin B (40 µM/ml, Sigma), which binds to glucose uptake transporter and inhibits glucose transport into the cell. Non-specific uptake was subtracted from total uptake to obtain specific uptake values.

Phosphorylation Studies

Differentiated C2C12 myotubes were pre-incubated with or without Ucn 2 peptide (0.1, 1 or 10 nM) for 1 hour prior to insulin treatment (10 nM, 5 min). Cells were harvested immediately in 100 µl of sample treatment buffer [STB, 50 mM Tris (pH 6.8), 100 mM dithiothreitol, 2% (wt/vol) sodium dodecyl sulfate, 0.1% (wt/vol) bromphenol blue, and 10% (wt/vol) glycerol]. The samples were boiled for 5 min, proteins were electrophoresed on 4-12% sodium dodecyl sulfate-polyacrylamide gradient gel (Invitrogen Life Technologies), subsequently transferred onto nitrocellulose membranes, and probed with antibodies specific for phosphorylated Akt (Ser 473, Cell Signaling Technology, Inc., Beverly, Mass.), phosphorylated ERK1/2-p42, 44 (Santa Cruz Biotechnology, Inc., Santa Cruz, Calif.), phosphorylated insulin receptor (Tyr 1146, Cell Signaling Technology, Inc.), or phosphorylated IRS1 (Ser 307, Upstate Cell Signaling Solutions, Lake placid, NY). The membranes were washed with phosphate buffer saline containing 0.05% (vol/vol) Tween 20 and incubated with horseradish peroxidase-conjugated anti mouse or rabbit IgG raised in sheep (Amersham Biotech Pharmacia). Immunoreactive proteins were visualized using Super Signal West Pico Chemiluminescent substrate (Pierce, Rockford, Ill.).

The relative protein levels were determined using densitometry (Image quant 1.2) by probing the membranes with antibodies directed against total proteins.

Example 5

CRFR2 Antagonism by Ucn 3 Reduces Islet Cell Insulin Secretion

To assess the effect of CRFR2 antagonism on islet cell function secretion of insulin from isolated rat islets was studied. As shown in FIG. 4a, pretreating rat islets with astressin-2B, a selective CRFR2 antagonist, attenuates 16.8 mM glucose-induced insulin secretion in a dose-dependent manner while the antagonist did not significantly modify insulin secretion induced by 8.4 mM glucose. Thus, activation of CRFR2 by endogenous ligands is involved in insulin secretion induced by high levels of glucose.

In order to determine the role of Ucn 3 in glucose induced insulin secretion, isolated rat islets were pretreated with an anti-Ucn 3 IgG prior to glucose treatment. As shown in FIG. 4b, anti-Ucn 3 antibodies (PBL #6570) attenuated glucose induced insulin secretion in a dose-dependent manner while normal rabbit IgG control had not effect on glucose-induced insulin secretion. These results indicate that Ucn 3, acts through CRFR2 and plays a role in stimulating glucose-induced insulin release.

The anti-Ucn 3 antibodies used for these experiments (PBL #6570) are generated by immunizing rabbits to human Gly-Try-Ucn 3 that is conjugated to human globulins via bisdiazotized benzidine.

Example 6

Ucn 3 is Involved in Glucose-Induced Insulin Secretion

Figure 5:
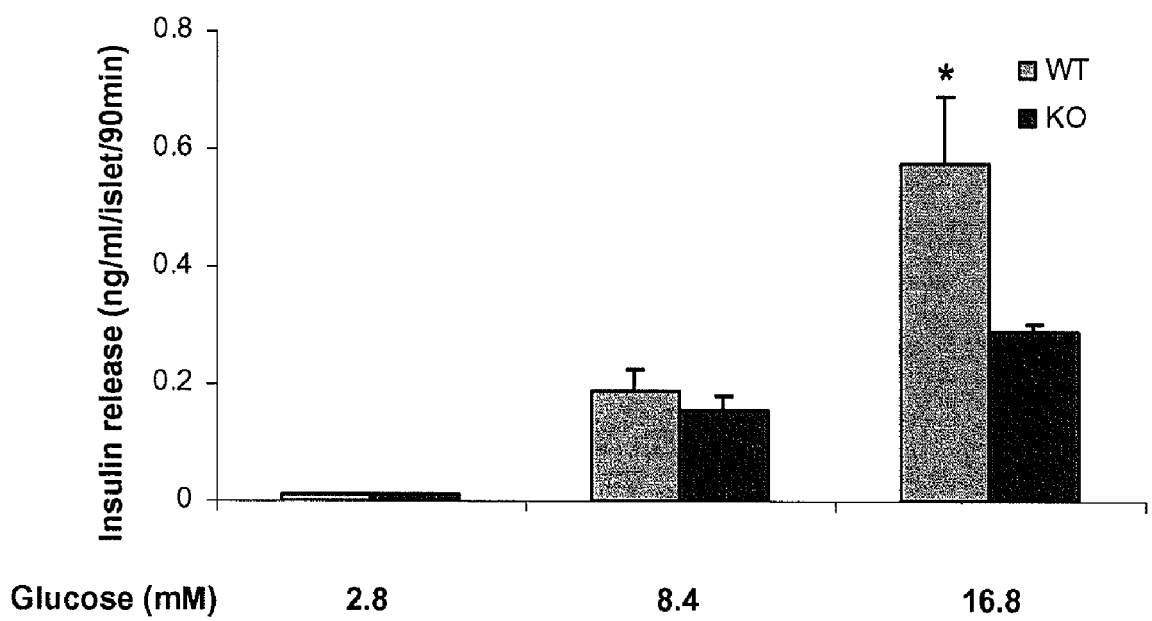
FIG. 5: Islets from Ucn 3 knock-out mice display reduced insulin secretion in response to glucose stimulation. Islet from Ucn 3 null mice were treated with increasing amounts of glucose as indicated on the x-axis and the concentration of insulin secreted per islet over a period of 90 minutes was calculated (y-axis). The asterisk indicates a statistically significant difference in insulin secretion between Ucn 3 null mouse islets and islets from wild type littermates.

To further investigate the role of Ucn 3 in insulin secretion islets isolated from male Ucn 3 null mice studied and compared to islets form wild-type littermates. Consistent with pharmacological studies, islets isolated from Ucn 3 null mice secreted significantly less insulin in response to 16.8 mM glucose as compared to the wild-type mice islets (FIG. 5). This data further confirms that Ucn 3 is important in mediating glucose-induced insulin secretion. Thus, under high nutrient states (at high glucose levels) Ucn 3 mediates an increased insulin secretion.

Example 7

Ucn 3 Stimulates Insulin Secretion In Vivo

Figure 6:
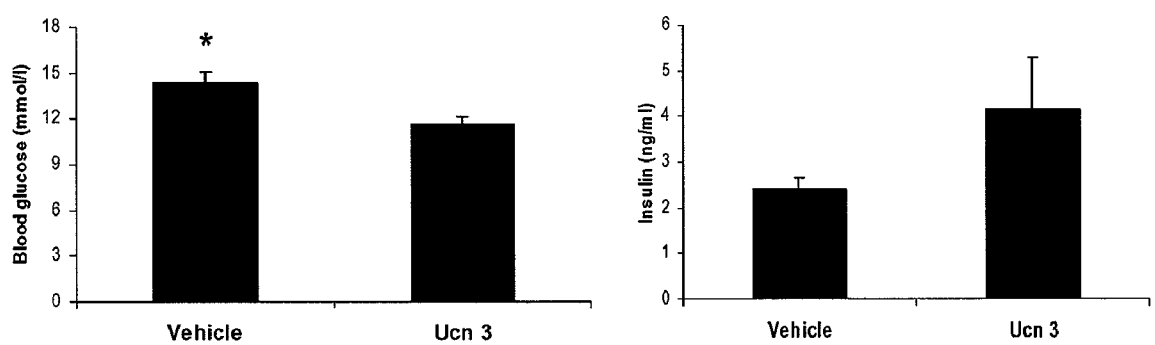
FIG. 6: The in vivo effect of Ucn 3 on insulin levels and blood glucose in a mouse model of type 2 diabetes. Wild-type mice were fed a high fat diet for 16 weeks to induce hyperglycemia. The mice were then injected for six days with vehicle alone or vehicle plus 30 μg/Kg of Ucn 3. Following treatment serum glucose (left panel) and serum insulin levels (right panel were determined.

As described in Example 2, mice feed a high fat diet are an accepted model for diabetes and exhibit the kind of high nutrient state in which Ucn 3 may regulate insulin levels. To directly assess the in vivo activity of Ucn 3 in this model system C57/B6 mice were fed with high fat diet (45% Kcal) for 16 weeks. The mice were then injected i.p. with either vehicle or mouse Ucn 3 (30 µg/kg) for 6 days. Interesting, mice treated with Ucn 3 had significantly lower glucose levels compared with the vehicle control (FIG. 6, left panel). Similarly, Ucn 3 treated mice also had higher insulin levels compared to the control, though the difference was not statistically significant (FIG. 6, right panel). These studies confirm the role of Ucn 3 in mediating increased insulin response to high blood sugar.

Example 8

Figure 7:
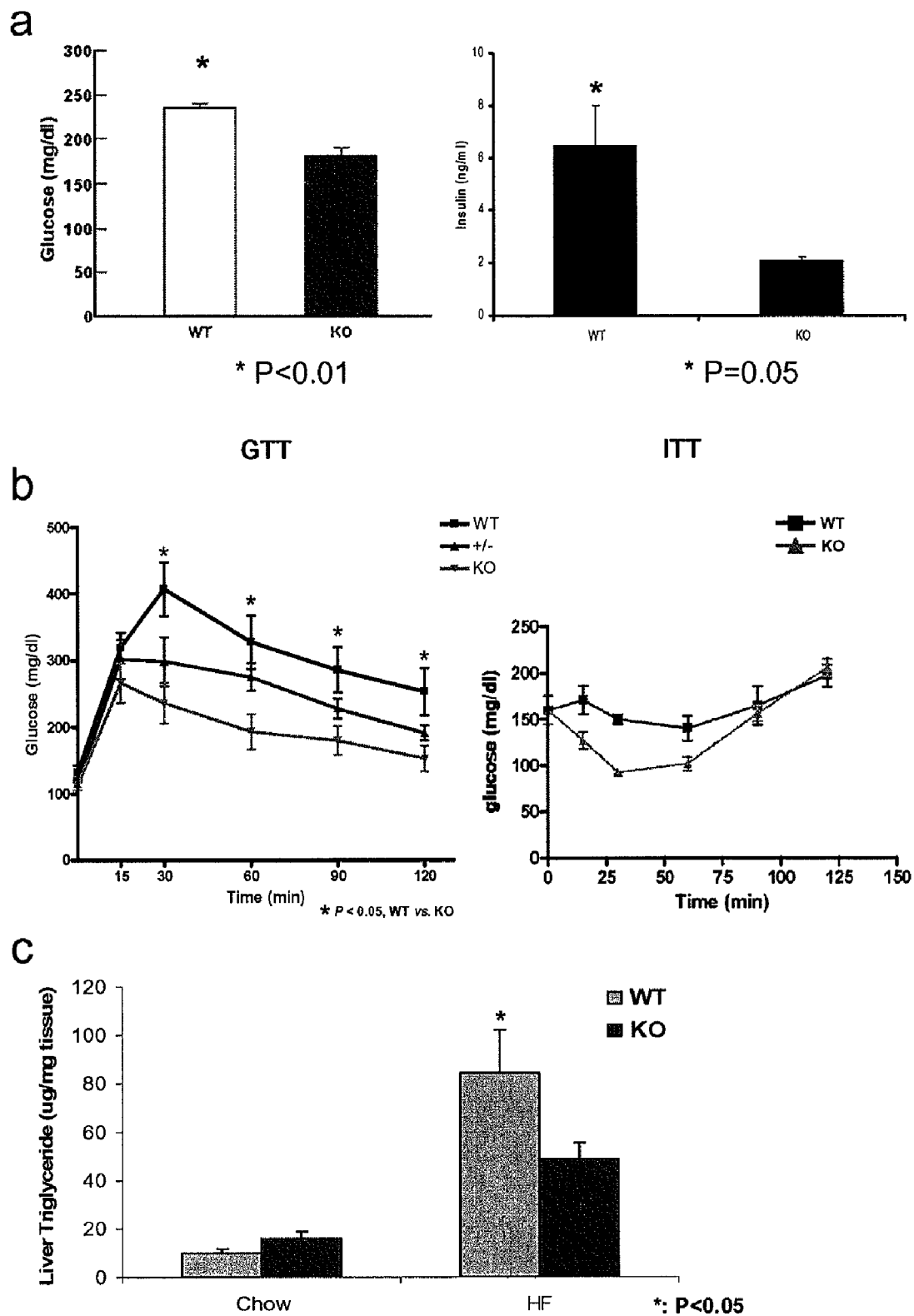
FIG. 7a-c: The detrimental effects of high fat diet are reduced in Ucn 3 null mice. Ucn 3 knock-out mice (KO) and wild-type littermates (WT) were fed a high fat diet for 16 weeks and the metabolic effects of the treatment was determined. (a) Serum glucose (left panel) and serum insulin (right panel) in wild type and Ucn 3 null mice following 16 weeks on the high fat diet. (b) Ucn 3 null and wild-type mice on high fat diet were subjected to glucose tolerance test (GTT, left panel) and Insulin tolerance test (ITT, right panel) as described in the examples. (c) The concentration of liver triglycerides was determined in wild type and Ucn 3 null mice following a normal (Chow) or high fat diet (HF).

Ucn 3 Contributes to Elevated Insulin and Glucose Levels in Mice on a High Fat Diet In order to investigate the role of Ucn 3 in mice with chronically elevated blood glucose Ucn 3 null and wild-type mice were fed a high fat diet (45% Kcal from fat) for 16 weeks. At the end of 16 week period plasma insulin and blood glucose were assessed. Significantly lower levels of both insulin (FIG. 7a, right panel) and glucose (FIG. 7a, left panel) were detected in the blood of mutant mice compared to the wild-type mice. Importantly, as shown in FIG. 7b, glucose tolerance and insulin tolerance tests (detailed in Example 1) showed that while the wild-type mice clearly developed hyperinsulinemia and insulin resistance, the mutant mice remained insulin sensitive. These data indicate that the absence of Ucn 3 protects the mice from developing chronic insulin resistance.

Additionally, it was determined that the liver of wild-type mice (on HFD) contained significantly more fat than the mutant mice as demonstrated in FIG. 7c that the wild-type mice liver has significantly higher triglyceride content than the Ucn 3 mutant mice. In fact, WT mice but not KO mice developed severe liver steatosis under HFD. Histological examination also confirmed that the liver of the WT mice had significantly more lipid accumulation than that of Ucn 3 KO.

Taken together, these studies indicate that Ucn 3 plays an important role in glucose-mediated insulin secretion. The effect of Ucn 3 on insulin secretion may explain the phenotype of Ucn 3 mutant mice under high fat diet. Loss of Ucn 3 under a high nutrient state will "clamp" the insulin at lower levels, which prevent animals from storing excess energy in various organs including the liver. Consequently the energy storing organs remain insulin sensitive under high nutrient state. It has been shown in many animal models that restriction of insulin action, either by food restriction (lower insulin levels) or by blocking insulin signaling, is beneficial to the health of the animals and can extend the life span of the animals. This is consistent with the finding that loss of Ucn 3 lowers an animal's ability to release insulin proportionally in response to excess energy intake and thus prevents the animal from developing overt diabetes under high fat feeding.

Example 9

Glucose Stimulates Ucn 3 Expression and Secretion

Figure 8:
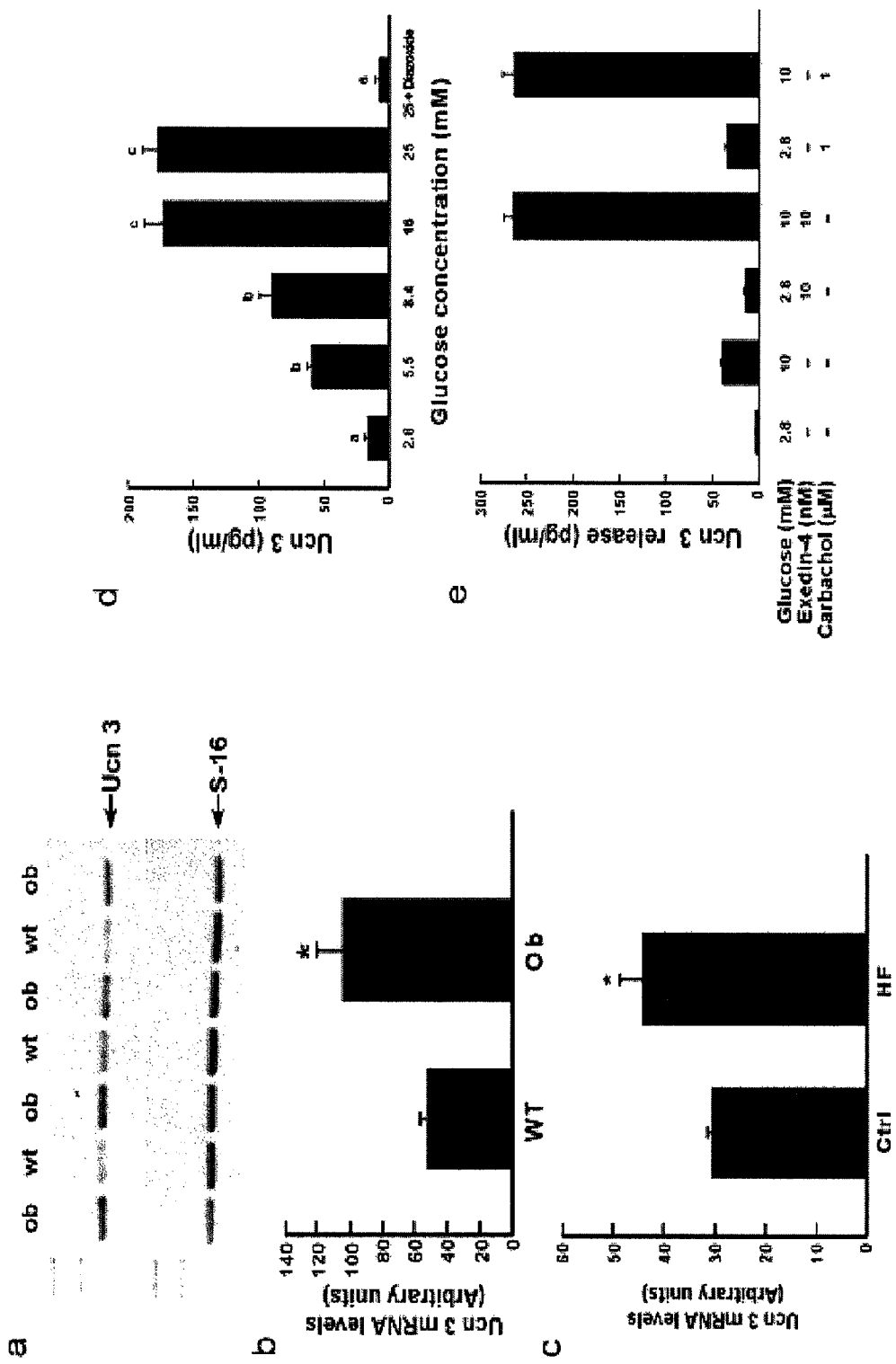
FIG. 8a-e: Elevation of pancreatic Ucn 3 expression in diabetic rodent models and stimulation of Ucn 3 release from β cells by glucose. (a) Representative agarose gel electrophoresis showing Ucn 3 and S-16 (control) PCR products. (b) Summary of Ucn 3 expression in ob/ob obese mice and the wildtype (WT) littermates. *: p<0.05 vs WT. (c) Ucn 3 mRNA levels in the pancreas of high fat fed rats (HF) and chow fed controls (Ctrl). *: p<0.05 vs Ctrl. (d) Ucn 3 secretion from MIN6 cells in response to various glucose concentrations. (e) Ucn 3 release from MIN6 cells, in response to glucose and/or insulin secretagogues. Values with different superscripts are significantly different with P<0.01.

To probe the physiological role of Ucn 3 in the pancreas, the expression of Ucn 3 mRNA in the pancreas was determined for of two diabetic models: ob/ob obese mice and rats fed with high fat diet (HFD). Briefly, to assess Ucn 3 mRNA levels total RNA was extracted from the pancreas and the cDNA products were used as templates for semiquantitative and RT-PCR analysis by using specific primers for Ucn 3 and the ribosomal protein S16 (as a control). Results indicate that Ucn 3 mRNA levels in the pancreas of ob/ob mice were significantly higher than the wildtype littermates (FIGS. 8a, b). Similarly, Ucn 3 mRNA levels were elevated in the pancreas of rats kept on HFD compared to rats fed with regular chow (FIG. 8c).

Ucn 3 secretion from P cells was studied using a mouse clonal P cell line, MIN6, as a model. For these studies MIN6 cells (Miyazaki et al., 1990) were cultured in DMEM supplemented with 10% fetal bovine serum (FBS), and 114 µm β-mercaptoethanol. To assess Ucn 3 secretion, the cells were seeded in 6-well plates and allowed to recover for 48 hrs. The cells were then washed twice with HEPES-balanced Krebs-Ringer bicarbonate buffer (HKRB) containing 5 mM glucose and 0.2% BSA and were incubated in HKRB with various testing reagents for 2 h at 37° C. The incubation buffer was collected and vacuum-dried for Ucn 3 RIA. Exendin-4 and diazoxide and carbachol were purchased from Phoenix Pharmaceuticals (Belmont, Calif.), and Sigma (St. Louis, Mo.), respectively. Results from these studies show that glucose stimulated Ucn 3 secretion in a dose-dependent manner (FIG. 8d). The effect of glucose on Ucn 3 secretion plateaued at 16.8 mM. Pretreating the cells with a KATP channel blocker, diazoxide (100 μM), effectively blocked glucose-induced Ucn 3 secretion (FIG. 8d), indicating that the effect of glucose on Ucn 3 secretion is mediated by the KATP channel. Several agents including glucagon-like peptide-1 (GLP-1) and acetylcholine have been shown to stimulate insulin secretion in a glucose dependent manner (Drucker, 2006; Gilon & Henquin, 2001). Treating MIN6 cells with exendin-4, a long acting GLP-1 analogue, or carbachol (a cholinergic agonist) induced minimal or moderate Ucn 3 secretion in the presence of 2.8 mM glucose (FIG. 8e). On the other hand, both exendin-4 and carbachol significantly stimulated Ucn 3 release in the presence of 10 mM glucose (FIG. 8e).

In summary pancreatic Ucn 3 mRNA levels are upregulated in obese and diabetic rodent models and Ucn 3 is secreted in conditions that are also stimulatory to insulin secretion, further indicating a role for Ucn 3 in insulin secretion stimulated by nutrient excess.

Example 10

The Effect of $Ast_2$-B on Insulin Secretion

Figure 9:
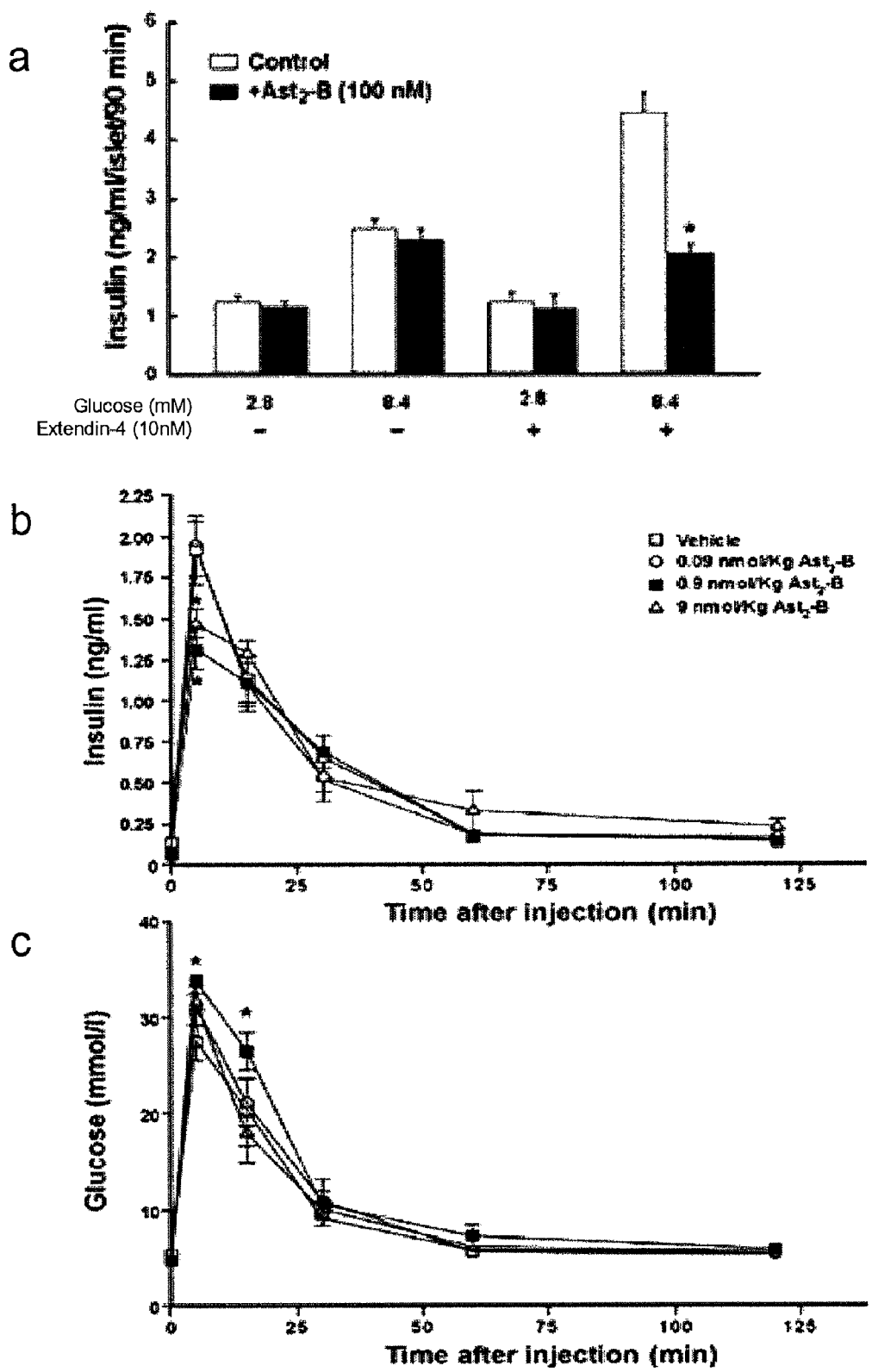
FIG. 9a-c: The effects of CRFR2 signaling on insulin secretion. (a) Islet insulin secretion induced by 16.8 mM glucose is attenuated by Ast2-B in a dose-dependent manner. **: p<0.01 vs. 16.8 mM glucose alone. Exendin-4 (10 nM) stimulated insulin release in the presence of 8.4 mM glucose however the effect was attenuated by Ast2-B. *: p<0.05 vs. exendin-4+8.4 mM glucose alone. (b-c) Blocking peripheral CRFR2 in vivo attenuates glucose induced insulin secretion. Plasma insulin (b) and glucose (c) levels in male rats treated with vehicle or Ast2-B (0.09-9 nmol/kg). *, P<0.05 vs. vehicle.
Figure 10:
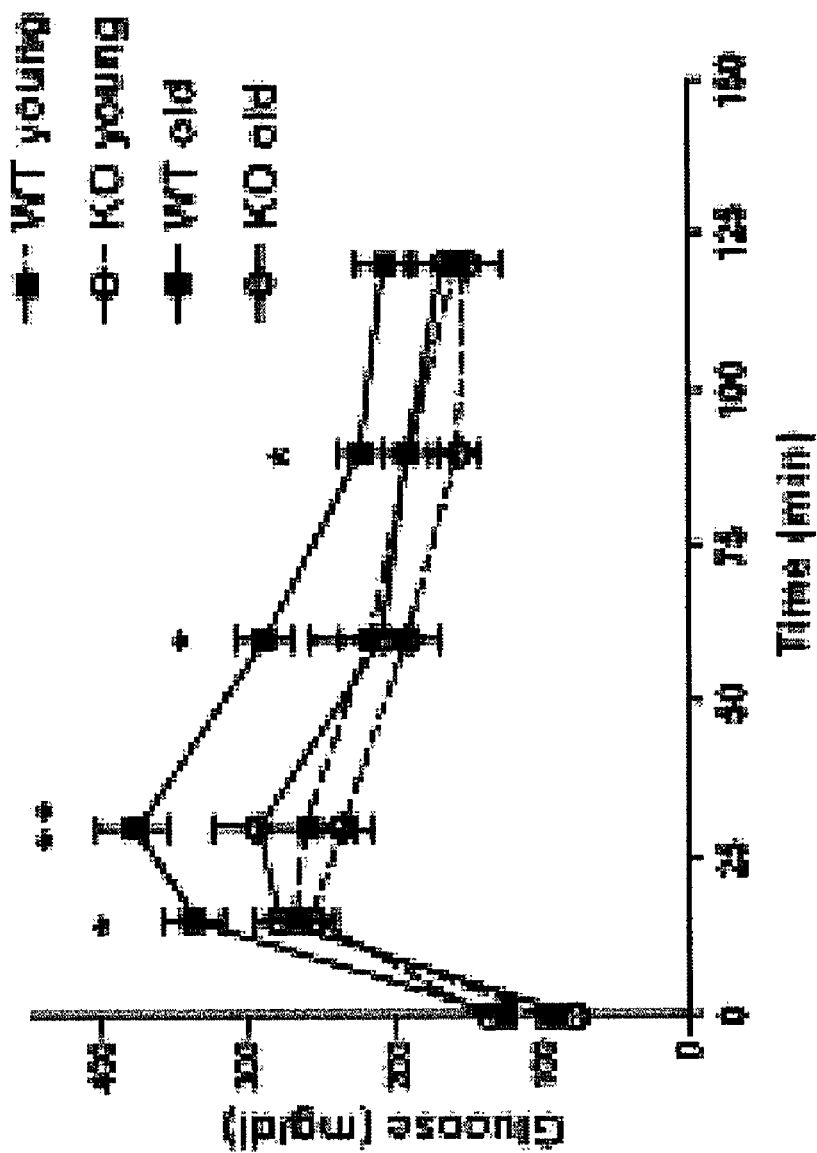
FIG. 10: Age dependent insulin resistance in Ucn 3 KO mice. Glucose tolerance tests in Ucn 3 KO and WT mice at 10-12 week old (young) and 12-13 months of age (old). *: $p<0.05$, and **: $p<0.01$ for old WT vs. old KO.

As shown in FIG. 4a, Ast2-B treatment did not affect insulin release induced by 2.8 or 8.4 mM glucose (or by 10 mM glucose). In contrast, Ast2-B significantly attenuated insulin release induced by 16.8 mM glucose in a dose dependent manner (FIG. 4a). The effect of CRFR2 receptors modulation on insulin secretion induced by GLP-1. was also tested. As shown in FIG. 9a, Exendin-4 significantly stimulated insulin release from isolated islets in the presence of 8.4 mM glucose and this effect was greatly attenuated by Ast2-B.

In order to determine whether blocking of CRFR2 function also modulates glucose induced insulin release in vivo, various doses of Ast2-B (0.09-9 nmol/kg) or vehicle were injected intravenously into male rats through a jugular vein cannula 20 min before injection of a glucose (2.8 mmol/kg) bolus. As shown in FIG. 9b, Ast2-B injection attenuated glucose-induced insulin secretion in a dose dependent manner, albeit the highest dose (9 nmol/kg) may be slightly less effective compared to the dose of 0.9 nmol/kg. Plasma glucose levels also mirrored the results of insulin (FIG. 9c). This result extends complements in vitro observations and suggests that endogenous CRFR2 in the periphery plays an important role in modulating insulin secretion. Although CRFR2 is also expressed in brain areas that are potentially involved in peripheral insulin secretion (Chalmers et al., 1995), the effect of Ast2-B on glucose-induced insulin secretion was probably due to a peripheral action since this peptide antagonist is unlikely to cross the blood brain barrier (Rivier et al., 2003).

Example 11

Ucn 3 KO Mice are Resistant Age Induced Insulin Resistance

It is widely known that advancing age is associated with impaired glucose handling and insulin resistance (Petersen et al., Science, 300:1140-2, 2003; Barbieri et al., Diabetes Metab Res Rev., 17:19-26, 2001). The protective effect observed in Ucn 3 mutant mice in high fat feeding suggested Ucn 3 mutant mice could remain insulin sensitive even in old age. We compared glucose tolerance in Ucn 3 mutant and age-matched wildtype littermates in 10-12 weeks old and again at 12-13 months of age. No differences were found in responses to glucose tolerance between the mutant and wildtype controls at younger ages (FIG. 11). In contrast, aged Ucn 3 null mice exhibited better glucose tolerance compared than did the wild-type controls (FIG. 11).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Appln. 2002/0168707
U.S. Appln. 2003/0051263
U.S. Appln. 2003/0055020
U.S. Appln. 2003/0159161
U.S. Appln. 2004/0064842
U.S. Appln. 2004/0265839
U.S. Appln. 2005/001416
U.S. application Ser. No. 11/199,821
U.S. application Ser. No. 11/350,411
U.S. Pat. No. 4,376,110
U.S. Pat. No. 4,554,101
U.S. Pat. No. 4,676,980
U.S. Pat. No. 4,676,980
U.S. Pat. No. 4,682,195
U.S. Pat. No. 4,683,202
U.S. Pat. No. 4,797,368
U.S. Pat. No. 4,816,567
U.S. Pat. No. 5,109,111
U.S. Pat. No. 5,139,941
U.S. Pat. No. 5,245,009
U.S. Pat. No. 5,510,458
U.S. Pat. No. 5,777,073
U.S. Pat. No. 5,874,227
U.S. Pat. No. 6,323,312
U.S. Pat. No. 6,506,559
U.S. Pat. No. 6,573,099
U.S. Pat. No. 6,569,620
U.S. Pat. No. 6,716,580
U.S. Pat. No. 6,806,084
U.S. patent Ser. No. 07/931,811
U.S. patent Ser. No. 07/934,373
Aguirre et al., *J. Biol. Chem.* 275:9047-9054, 2000.
Bale et al., *Endocrinology,* 144:2580-2587, 2003.

Barbieri et al., *Diabetes Metab Res Rev.*, 17:19-26, 2001.
Bhatia, *South Med. J*, 98:903-910, 2005.
Bouche et al., *Endocr. Rev.*, 25:807-837, 2004.
Brodeur et al., In: *Monoclonal antibody production techniques and applications*, Marcel Dekker, Inc., NY, 51-63, 1987.
Brown et al., *Endocrinology*, 111:928-931, 1982.
Bugianesi et al., *Hepatology*, 42:987-1000, 2005.
Campbell et al., *Ann. Pharmacother.*, 30:1255-1262, 1996.
Chalmers et al., *J. Neuroscience*, 15:6340-6350, 1995.
Chen et al., *Endocrinology*, 145:2445-2457, 2004.
Chen et al., *Mol. Endocrinol.*, 19:441-458, 2005.
Clackson et al., *Nature*, 352:624-628, 1991.
Couch et al., *Am. Rev. Resp. Dis.*, 88:394-403, 1963.
Coupar et al., *Gene*, 68:1-10, 1988.
Dallman et al., *Ann. N.Y. Acad. Sci.*, 771:730-742, 1995.
David et al., *Biochemistry*, 13:1014, 1974.
De Kloet, *Ann. N.Y. Acad. Sci.*, 1018:1-15, 2004.
Drucker, *Cell Metab.*, 3:153-65, 2006
European Appln. 03089
Evans et al., *Nat. Med.*, 10:355-361, 2004.
Florence and Yeager, *Amer. Fam. Phys.*, 59(10):2835-2844, 2849-2850, 1999.
Fingl et al., In: *The Pharmacological Basis of Therapeutics*, 1:1, 1975.
Freireich et al., *Cancer Chemother. Reports*, 50:219-244, 1966.
Friedman, *Nat. Med.*, 10:563-569, 2004.
Gilon & Henquin, *Endocr. Rev.*, 22:565-604, 2001
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Goding, In: *Monoclonal Antibodies: Principles and Practice*, 2d ed., Academic Press, Orlando, Fla., pp 60-61, 71-74, 1986.
Griffith et al., *EMBO J.*, 12:725-734, 1993.
Gual et al., *Biochimie.*, 87:99-109, 2005.
Hsu and Hsueh, *Nat. Med.*, 7:605-611, 2001.
Hunter et al., *Nature*, 144:945, 1962.
Inzucchi et al., *N. Engl. J. Med.*, 338:867-872, 1998.
Jakobovits et al., *Nature*, 362:255-258, 1993.
Jakobovits et al., *Proc. Natl. Acad. Sci. USA*, 90:2551-255, 1993.
Johnson et al., *Curr. Opinion Struct. Biol.*, 3:564-571, 1993.
Jones et al., *Nature*, 321:522-525, 1986.
Karlsson et al., *EMBO J.*, 5:2377-2385, 1986.
Kishimoto et al., *Proc. Natl. Acad. Sci. USA*, 92:1108-1112, 1995.
Kohler and Milstein, *Nature*, 256:495-497, 1975.
Kostich et al., *Mol. Endo.*, 12(8):1077-1085, 1998
Kozbor, *J. Immunol.*, 133(6):3001-3005, 1984.
Kyte and Doolittle, *J. Mol. Biol.*, 157(1):105-132, 1982.
Laughlin et al., *J. Virol.*, 60(2):515-524, 1986.
Mahmood et al., *J. Clin. Pharmacol.*, 43:692-697, 2003.
Maniatis, et al., *Molecular Cloning, A Laboratory Manual*, Cold Spring Harbor Press, Cold Spring Harbor, N.Y., 1990.
Marks et al., *Bio/Technol.*, 10:779-783, 1992.
Marks et al., *J. Mol. Biol.*, 222:581-597, 1991.
McCafferty et al., *Nature*, 348:552-553, 1990.
Millstein and Cuello, *Nature*, 305:537-539, 1983.
Miyazaki et al., *Endocrinology*, 127:126-132, 1990.
Morrison et al., *Proc. Nat. Acad. Sci. USA*. 81:6851, 1984.
Munson and Pollard, *Anal. Biochem.*, 107:220, 1980.
Nagy and Clair, *Obes. Res.*, 8:392-398, 2000.
Nygren, *Histochem. and Cytochem.*, 30:407, 1982.
Pain et al., *J. Immunol. Meth.*, 40:219, 1981.
PCT Appln. WO 91/00360
PCT Appln. WO 92/200373
PCT Appln. WO 93/06213
PCT Appln. WO 93/08829
Perrin and Vale, *Ann. NY Acad. Sci.*, 885:312-328, 1999.
Perrin et al., *Proc. Natl. Acad. Sci. USA*, 92:2969-2973, 1995.
Petersen et al., *Science*, 300:1140-2, 2003.
Remington's Pharmaceutical Sciences" 15th Edition, pages 1035-1038 and 1570-1580, 1990.
Reyes et al., *Proc. Natl. Acad. Sci. USA*, 98:2843-2848, 2001.
Riechmann et al., *Nature*, 332:323-327, 1988.
Rivier et al., *J. Med. Chem.*, 45:4737-4747, 2002.
Rivier et al., *Endocrinology*, 144:2396-403, 2003.
Sambrook et al., In: *Molecular cloning*, Cold Spring Harbor Laboratory Press, Cold Spring Harbor, N.Y., 2001.
Scheen, *Drugs*, 54:355-368, 1997.
Seely and Olefsky, In: *Insulin Resistance*, Wiley, New York, 187-252, 1993.
Shulman et al., *N. Engl. J. Med.*, 322:223-228, 1990.
Shulman, *J. Clin. Invest.*, 106:171-176, 2000.
Shulman, *Physiology*, 19:183-190, 2004.
Smith et al., *Neuron.*, 20:1093-1102, 1998.
Sparano and Seaton, *Pharmacotherapy*, 18:539-548, 1998.
Spiegelman and Flier, *Cell*, 104:531-543, 2001.
Suresh et al., *Methods in Enzymology*, 121:210-228, 1986.
Top et al., *J. Infect. Dis.*, 124:155-160, 1971.
Traunecker et al., *EMBO*, 10:3655-3659, 1991.
Vaag et al., *J. Clin. Invest.*, 89:782-788, 1992.
Verhoeyen et al., *Science*, 239:1534-1536, 1988.
Virkamaki et al., *J. Clin. Invest.*, 103:931-943, 1999.
Warram et al., *Ann. Intern. Med.*, 113:909-915, 1990.
Watanabe et al. *Risk Analysis*, 12:301-310, 1992.
Waterhouse et al., *Nucl. Acids Res.*, 21:2265-2266, 1993.
Zierath and Wallberg-Henriksson, *Ann. NY. Acad. Sci.*, 967: 120-134, 2002.
Zierath et al., *Diabetologia*, 43:821-835, 2000.
Zola, In: *Monoclonal Antibodies: A Manual of Techniques*, CRC Press, Inc., pp. 147-158, 1987.

What is claimed is:

1. A method for increasing insulin sensitivity or decreasing insulin secretion in a subject in need of such therapy, comprising administering to a subject with a reduced insulin sensitivity or an increased serum insulin level an amount of a composition comprising an antibody that is effective to reduce CRFR2 signaling.

2. The method of claim 1, wherein the subject is a human.

3. The method of claim 1, wherein CRFR2 signaling is reduced in skeletal muscle cells.

4. The method of claim 1, wherein the antibody binds to and inhibits CRFR2.

5. The method of claim 1, wherein the molecule that binds to CRFR2 is an antibody that binds Ucn 2 and inhibits its binding to CRFR2.

6. The method of claim 1, wherein the antibody is a polyclonal antibody, Fab fragment, monoclonal antibody, single chain antibody, or a humanized or partially humanized version of one of the foregoing.

7. The method of claim 1, wherein insulin secretion in the subject is decreased following administration of the CRFR2 antagonist.

8. The method of claim 7, wherein decreasing insulin secretion in the subject reduces a serum insulin level in the subject.

9. The method of claim 7, wherein decreasing insulin secretion in the subject comprises decreasing glucose-induced insulin secretion in the subject.

10. The method of claim 1, wherein insulin-sensitivity in the subject is decreased following administration of the CRFR2 antagonist.

11. The method of claim 1, wherein the subject suffers from type 2 diabetes.

12. The method of claim 1, wherein the mass of adipose tissue in the subject is reduced following administration of the CRFR2 antagonist.

13. The method of claim 1, further comprising increasing the mass of lean tissue in the subject.

14. The method of claim 1, wherein the subject suffers from Metabolic Syndrome.

15. The method of claim 1, wherein the subject suffers from nonalcoholic fatty liver disease.

16. The method of claim 1, wherein the subject suffers from polycystic ovarian syndrome.

* * * * *

UNITED STATES PATENT AND TRADEMARK OFFICE
CERTIFICATE OF CORRECTION

PATENT NO. : 7,815,905 B2  Page 1 of 1
APPLICATION NO. : 11/668047
DATED : October 19, 2010
INVENTOR(S) : Alon M. Chen et al.

It is certified that error appears in the above-identified patent and that said Letters Patent is hereby corrected as shown below:

In column 1, lines 10-13, delete paragraph and insert
--This invention was made with government support under grant number DK 26741 awarded by the National Institute of Diabetes and Digestive and Kidney Diseases (NIDDK). The government has certain rights in the invention.--.

Signed and Sealed this
Eleventh Day of January, 2011

David J. Kappos
*Director of the United States Patent and Trademark Office*